US010039850B2

(12) United States Patent
Taggart et al.

(10) Patent No.: US 10,039,850 B2
(45) Date of Patent: Aug. 7, 2018

(54) STERILIZATION DEVICE AND METHODS

(71) Applicant: STERIO3, LLC, Madison, WI (US)

(72) Inventors: Daniel S. Taggart, Salt Lake City, UT (US); Jessica I. McKelvie, Salt Lake City, UT (US); James J. Steppan, Park City, UT (US); Thomas R. Hinklin, Sandy, UT (US); Chett J. Boxley, Park City, UT (US)

(73) Assignee: STERIO3, LLC, Madison, WI (US)

( * ) Notice: Subject to any disclaimer, the term of this patent is extended or adjusted under 35 U.S.C. 154(b) by 0 days.

(21) Appl. No.: 15/649,447

(22) Filed: Jul. 13, 2017

(65) Prior Publication Data

US 2017/0304476 A1 Oct. 26, 2017

Related U.S. Application Data

(63) Continuation-in-part of application No. 15/406,363, filed on Jan. 13, 2017, now Pat. No. 9,849,204.
(Continued)

(51) Int. Cl.
*A61L 2/00* (2006.01)
*G05B 1/00* (2006.01)
(Continued)

(52) U.S. Cl.
CPC .................... *A61L 2/22* (2013.01); *A61L 2/24* (2013.01); *A61L 2202/11* (2013.01);
(Continued)

(58) Field of Classification Search
CPC ........ A61L 2/00; A61L 2/0088; A61L 2/0094; A61L 2/186; A61L 2/202; A61L 2/208
(Continued)

(56) References Cited

U.S. PATENT DOCUMENTS 3,704,096 A 11/1972 Karlson et al.
4,372,916 A 2/1983 Chamberlain et al.
(Continued)

FOREIGN PATENT DOCUMENTS

CN 2905066 5/2007
KR 20120093790 A 8/2012
(Continued)

OTHER PUBLICATIONS

Fischbacher, et al., "The OH Radical Yield in the H2O2 O3 (Peroxone) Reaction," Environmental Science and Technology, vol. 47, Jul. 24, 2013, pp. 9959-9964.
(Continued)

*Primary Examiner* — Monzer R Chorbaji
(74) *Attorney, Agent, or Firm* — Foley & Lardner LLP

(57) ABSTRACT

Embodiments of the present disclosure generally relate to devices and methods for sterilizing equipment. More particularly, one or more embodiments described in the present disclosure are directed to portable devices for sterilizing medical equipment in emergency situations. The sterilization devices and method of the present disclosure address an unmet need for sterilizing surgical equipment in a manner that is not only effective and time-efficient, but is also portable and reliable enough to use in emergency medical situations in remote locations where modern sterilization equipment is not available.

17 Claims, 26 Drawing Sheets

Related U.S. Application Data

(60) Provisional application No. 62/278,180, filed on Jan. 13, 2016.

(51) Int. Cl.
*A61L 9/00* (2006.01)
*G01D 11/26* (2006.01)
*A61L 2/22* (2006.01)
*A61L 2/24* (2006.01)

(52) U.S. Cl.
CPC ..... *A61L 2202/122* (2013.01); *A61L 2202/14* (2013.01); *A61L 2202/15* (2013.01); *A61L 2202/16* (2013.01); *A61L 2202/24* (2013.01)

(58) Field of Classification Search
USPC .............. 422/1, 28, 105, 119, 292, 305
See application file for complete search history.

(56) References Cited

U.S. PATENT DOCUMENTS

| | | | |
|---|---|---|---|
| 4,550,010 A | 10/1985 | Chelu | |
| 4,642,165 A | 2/1987 | Bier | |
| 4,643,876 A | 2/1987 | Jacobs et al. | |
| 5,207,237 A | 5/1993 | Langford | |
| 5,266,275 A | 11/1993 | Faddis | |
| 5,520,893 A | 5/1996 | Kasting et al. | |
| 5,525,310 A | 6/1996 | Decker et al. | |
| 5,527,508 A | 6/1996 | Childers et al. | |
| 5,667,753 A | 9/1997 | Jacobs et al. | |
| 5,700,426 A | 12/1997 | Schmitthaeusler et al. | |
| 5,855,856 A | 1/1999 | Karlson | |
| 5,904,901 A * | 5/1999 | Shimono .............. | A61L 9/015 422/120 |
| 5,942,438 A | 8/1999 | Antonoplos et al. | |
| 6,096,266 A | 8/2000 | Duroselle | |
| 6,156,267 A | 12/2000 | Pai et al. | |
| 6,365,103 B1 | 4/2002 | Fournier | |
| 6,410,338 B1 | 6/2002 | Lippold et al. | |
| 6,589,479 B2 | 7/2003 | Dufresne et al. | |
| 6,630,105 B1 | 10/2003 | O'Neill et al. | |
| 6,699,434 B1 | 3/2004 | Lukasik et al. | |
| 6,767,509 B1 | 7/2004 | Griesbach et al. | |
| 7,048,887 B2 | 5/2006 | Frost et al. | |
| 7,128,872 B2 | 10/2006 | Robitaille et al. | |
| 7,186,371 B1 | 3/2007 | Watling | |
| 7,582,257 B2 | 9/2009 | Bedard et al. | |
| 7,588,720 B2 | 9/2009 | Turcot et al. | |
| 7,608,217 B2 | 10/2009 | Champagne | |
| 7,892,486 B2 * | 2/2011 | Mizuno .............. | A61L 2/14 422/33 |
| 8,529,832 B2 | 9/2013 | Lee | |
| 8,540,943 B2 | 9/2013 | Kee et al. | |
| 8,683,401 B2 | 3/2014 | Onodera | |
| 8,841,440 B2 | 9/2014 | Chu et al. | |
| 8,945,467 B2 | 2/2015 | Soberon et al. | |
| 2002/0012610 A1 | 1/2002 | Dufresne et al. | |
| 2003/0196678 A9 | 10/2003 | Torek et al. | |
| 2004/0077917 A1 | 4/2004 | Centanni et al. | |
| 2005/0147527 A1 | 7/2005 | Brown et al. | |
| 2006/0099121 A1 | 5/2006 | Doona et al. | |
| 2007/0065335 A1 | 3/2007 | Bedard et al. | |
| 2007/0221582 A1 | 9/2007 | Holland et al. | |
| 2007/0231199 A1 | 10/2007 | Lin et al. | |
| 2008/0014113 A1 | 1/2008 | Centanni | |
| 2008/0233002 A1 | 9/2008 | Mizuno et al. | |
| 2011/0076191 A1 | 3/2011 | Gordon et al. | |
| 2011/0076192 A1 | 3/2011 | Robitaille et al. | |
| 2011/0085934 A1 | 4/2011 | Joshi et al. | |
| 2013/0236355 A1 | 9/2013 | Dufresne et al. | |
| 2013/0243649 A1 | 9/2013 | Dufresne et al. | |
| 2015/0352238 A1 | 12/2015 | Dufresne et al. | |

FOREIGN PATENT DOCUMENTS

| | | |
|---|---|---|
| WO | WO-2005/035067 A2 | 4/2005 |
| WO | WO-2015/135887 A1 | 9/2015 |
| WO | WO-2016/025934 A1 | 2/2016 |

OTHER PUBLICATIONS

International Search Report and Written Opinion issued in PCT Application No. PCT/US2017/013525 dated Apr. 28, 2017 (12 pages).
James, Patrick, "Improved Electrolytic Hydrogen Peroxide Generator," www.defensetechbriefs.com, Jul. 1, 2005, 1 page.
Non-Final Rejection on U.S. Appl. No. 15/406,363 dated Apr. 20, 2017 (10 pages).
Sterizone VP4 Sterilizer, TSO3 Inc., Quebec, Canada, acquired Apr. 24, 2015, 28 pages.
U.S. Notice of Allowance dated Aug. 16, 2017.

* cited by examiner

STERILIZATION DEVICE AND METHODS

CROSS-REFERENCE TO RELATED APPLICATIONS

This application is a continuation-in-part of prior application Ser. No. 15/406,363 filed Jan. 13, 2017 and entitled "STERILIZATION DEVICE AND METHODS," which claims the benefit of U.S. Provisional Application No. 62/278,180, filed Jan. 13, 2016 and entitled "STERILIZATION DEVICE AND METHOD." The foregoing applications are incorporated herein by reference in their entireties for all purposes.

STATEMENT REGARDING FEDERALLY SPONSORED RESEARCH OR DEVELOPMENT

Some embodiments of the invention originally disclosed in relation to prior application Ser. No. 15/406,363 were made with government support under Grant No. FA8650-13-C-6376 awarded by the Department of Defense. The U.S. Government has certain rights in those previously disclosed embodiments of the invention. Embodiments of the invention originally disclosed herein were not made with government support and the U.S. Government does not have rights in those embodiments.

BACKGROUND OF THE INVENTION

1. Field of the Invention

Embodiments of the present disclosure generally relate to devices and methods for sterilizing medical equipment. In particular, the present disclosure provides portable devices for sterilizing surgical equipment, such as in emergency medical situations, as well as in remote locations where modern sterilization equipment is not available.

2. Background and Related Art

Contaminated surgical equipment can result in secondary complications ranging from surgical site infections to death. Consequently, surgeons require effective and dependable sterilization devices to ensure that their surgical equipment and instruments are sterile. In many cases, it is also important that sterilization devices effectively sterilize surgical equipment in a timely manner, especially in emergency medical situations such as natural disasters and battlefields. Current sterilization devices typically use steam sterilization, which has several drawbacks that make these devices and methods unsuitable for use in emergency medical situations, including the requirement for potable water, access to a power source, and a lack of portability. Therefore, there is a need for improved devices and methods for sterilizing surgical equipment in a manner that is not only effective and time-efficient, but also provides sufficient portability and reliability to use in emergency medical situations in remote locations where modern sterilization equipment may not available.

BRIEF SUMMARY OF THE INVENTION

Implementation of the present disclosure provides portable sterilization devices, methods for manufacturing portable sterilization devices, and methods for using portable sterilization devices to sterilize surgical equipment, surgical instruments, and the like. According to certain implementations of the disclosure, a portable sterilization device for use with one or more sterilants includes a sealable sterilization chamber having one or more walls defining a sealable internal volume having a height, a width, and a depth. The portable sterilization device also includes a sterilant delivery device having an aerosolizing component and a sterilant outlet, the sterilant outlet being disposed within or at a boundary of the internal volume and oriented to disperse aerosolized sterilant into the internal volume and an ozone delivery device having an ozone outlet disposed within or at the boundary of the internal volume such that ozone is delivered to the internal volume. The portable sterilization device also includes a control panel operable to activate the sterilant delivery device and the ozone delivery device when the sterilization chamber is sealed, whereby an oxidative aerosol sterilant is created within the internal volume by mixing of the aerosolized sterilant and the ozone in the internal volume of the sealable sterilization chamber, and wherein the sterilant is substantially prevented from mixing with ozone prior to being dispersed through the sterilant outlet into the internal volume by the sterilant delivery device.

The portable sterilization device may also include an ozone generation assembly and an airflow circulation assembly. The airflow circulation assembly may include an air pump, an air return in fluid communication with the ozone generation assembly, the air return having an air return opening in fluid communication with the internal volume of the sterilization chamber, and an ozone supply feed in fluid communication with the ozone generation assembly and the ozone outlet.

The airflow circulation assembly may optionally include a plurality of air return openings in fluid communication with the air return and the internal volume of the sterilization chamber. The sterilant outlet, the ozone outlet, and the air return opening may be located within or at the boundary of the internal volume so as to optimize formation of the oxidative aerosol sterilant within the internal volume. Each of the sterilant outlet, the ozone outlet, and the air return opening may be located on walls of the sealable sterilization chamber such as a top wall, a bottom wall, and a side wall.

The sterilant delivery device may include a plurality of sterilant outlets disposed within or at the boundary of the internal volume of the sterilization chamber, the plurality of sterilant outlets being located and oriented so as to disperse an effective amount of aerosolized sterilant to an entirety of a treatment volume within the internal volume of the sterilization chamber. The treatment volume is defined as the portion of the internal volume of the sterilization chamber adapted to receive surgical instruments or other objects to be sterilized, less the gas-impermeable volume taken up by such surgical instruments or other objects to be sterilized. In other words, the treatment volume is the gas-permeable volume of the internal volume of the sterilization chamber in which surgical instruments or other objects to be sterilized may be placed, and represents the volume in which a reasonable assurance of sterility after treatment may be assured. In some instances, the treatment volume may be coextensive with the internal volume of the sterilization chamber less the gas-impermeable volume of the objects being sterilized and less any protrusions represented by structures of one or more of the sterilant outlet(s) and/or sterilant delivery device(s), the ozone outlet(s) and/or ozone delivery device(s), and/or air return inlet(s) present within the internal volume of the sterilization chamber.

The ozone delivery device may include an ozone source in fluid communication with a plurality of ozone outlets through a manifold, the plurality of ozone outlets being disposed within or at the boundary of the internal volume of the sterilization chamber, the plurality of ozone outlets being located and oriented so as to disperse ozone to an entirety of the treatment volume within the internal volume of the sterilization chamber. Where the ozone delivery device includes a plurality of ozone outlets, the sterilant delivery device may include a plurality of sterilant outlets disposed within or at the boundary of the internal volume of the sterilization chamber, the plurality of sterilant outlets being located and oriented so as to disperse an effective amount of aerosolized sterilant to an entirety of the treatment volume within the internal volume of the sterilization chamber. The plurality of sterilant outlets and the plurality of ozone outlets may be interspersed to facilitate mixing of the aerosolized sterilant and the ozone within the internal volume of the sterilization chamber. In some instances, at least a portion of the plurality of sterilant outlets and at least a portion of the plurality of ozone outlets may be incorporated into or form a pin mat disposed within the internal volume of the sterilization chamber, the pin mat being adapted to support an object to be sterilized in the portable sterilization device.

The sterilant may be or include hydrogen peroxide.

The aerosolizing component may be a component such as an ultrasonic nebulizer, a mechanical nebulizer, a piezoelectric nebulizer, a compressive nebulizer, a misting nozzle supplied by a pump, a misting nozzle supplied by a linear actuator, an ultrasonic spray nozzle, a Venturi nozzle, a microfluidic pin orifice, an air atomizing nozzle, a heat vaporizer, or a diesel fuel injector.

According to further implementations of the disclosure, a portable sterilization device for use with one or more sterilants includes a sealable sterilization chamber having one or more walls defining a sealable internal volume having a height, a width, and a depth and a sterilant delivery device comprising an aerosolizing component and a sterilant outlet, the sterilant outlet being disposed within or at a boundary of the internal volume and oriented to disperse aerosolized sterilant into the internal volume. The portable sterilization device also includes an ozone generation and airflow circulation assembly comprising a fluid loop for circulating fluids through the sterilization chamber. The ozone generation and airflow circulation assembly includes an air return having an air return opening in fluid communication with the internal volume of the sterilization chamber, an ozone generation assembly having a fluid intake that receives fluid removed from the sterilization chamber through the air return, an ozone supply feed that receives ozone from the ozone generation assembly, and a plurality of ozone outlets in fluid connection with the ozone supply feed through a manifold, the plurality of ozone outlets being disposed within or at the boundary of the sterilization chamber so as to be capable of dispersing ozone to an entirety of a treatment volume of the internal volume of the sterilization chamber. The portable sterilization device also includes a control panel operable to activate the sterilant delivery device and the ozone generation and airflow circulation assembly when the sterilization chamber is sealed, whereby an oxidative aerosol sterilant is created within the internal volume by mixing of the aerosolized sterilant and the ozone in the internal volume of the sealable sterilization chamber, and wherein the sterilant is substantially prevented from mixing with ozone prior to being dispersed through the sterilant outlet into the internal volume by the sterilant delivery device.

The treatment volume is defined as the portion of the internal volume of the sterilization chamber adapted to receive surgical instruments or other objects to be sterilized, less the gas-impermeable volume taken up by such surgical instruments or other objects to be sterilized. In other words, the treatment volume is the gas-permeable volume of the internal volume of the sterilization chamber in which surgical instruments or other objects to be sterilized may be placed, and represents the volume in which a reasonable assurance of sterility after treatment may be assured. In some instances, the treatment volume may be coextensive with the internal volume of the sterilization chamber less the gas-impermeable volume of the objects being sterilized and less any protrusions represented by structures of one or more of the sterilant outlet(s) and/or sterilant delivery device(s), the ozone outlet(s) and/or ozone delivery device(s), and/or air return inlet(s) present within the internal volume of the sterilization chamber.

The ozone generation and airflow circulation assembly optionally includes a plurality of air return openings in fluid communication with the air return and the internal volume of the sterilization chamber. Additionally, the sterilant delivery device optionally includes a plurality of sterilant outlets disposed within or at the boundary of the internal volume of the sterilization chamber, the plurality of sterilant outlets being located and oriented so as to disperse aerosolized sterilant to an entirety of the treatment volume within the internal volume of the sterilization chamber. The plurality of sterilant outlets and the plurality of ozone outlets may be interspersed to facilitate mixing of the aerosolized sterilant and the ozone within the internal volume of the sterilization chamber. At least a portion of the plurality of sterilant outlets and at least a portion of the plurality of ozone outlets may be incorporated into or form a pin mat disposed within the internal volume of the sterilization chamber, the pin mat being adapted to support an object to be sterilized in the portable sterilization device.

According to additional implementations of the disclosure, a method includes manufacturing a portable sterilization device. The portable sterilization device so manufactured includes a sealable sterilization chamber having one or more walls defining a sealable internal volume having a height, a width, and a depth. The portable sterilization device also includes a sterilant delivery device having an aerosolizing component and a sterilant outlet, the sterilant outlet being disposed within or at a boundary of the internal volume and oriented to disperse aerosolized sterilant into the internal volume and an ozone delivery device having an ozone outlet disposed within or at a boundary of the internal volume such that ozone is delivered to the internal volume. The portable sterilization device also includes a control panel operable to activate the sterilant delivery device and the ozone delivery device when the sterilization chamber is sealed, whereby an oxidative aerosol sterilant is created within the internal volume by mixing of the aerosolized sterilant and the ozone in the internal volume of the sealable sterilization chamber, and wherein the sterilant is substantially prevented from mixing with ozone prior to being dispersed through the sterilant outlet into the internal volume by the sterilant delivery device.

According to the manufacturing method, the ozone delivery device may include an ozone source in fluid communication with a plurality of ozone outlets through a manifold, the plurality of ozone outlets being disposed within or at the boundary of the internal volume of the sterilization chamber, the plurality of ozone outlets being located and oriented so as to disperse ozone to an entirety of the treatment volume of the internal volume of the sterilization chamber, and wherein the sterilant delivery device comprises a plurality of sterilant outlets disposed within or at the boundary of the internal volume of the sterilization chamber, the plurality of sterilant outlets being located and oriented so as to disperse aerosolized sterilant to an entirety of the treatment volume within the internal volume of the sterilization chamber. The plurality of sterilant outlets and the plurality of ozone outlets may be interspersed to facilitate mixing of the sterilant and the ozone within the internal volume of the sterilization chamber, and at least a portion of the plurality of sterilant outlets and at least a portion of the plurality of ozone outlets may be incorporated into or form a pin mat disposed within the internal volume of the sterilization chamber, the pin mat being adapted to support an object to be sterilized in the portable sterilization device.

According to additional implementations of the disclosure, a sterilization method utilizes a portable sterilization device in accordance with implementations of the disclosure discussed herein. A sterilization method includes steps of placing an object to be sterilized within a sealable sterilization chamber of a portable sterilization device and sealing the sterilization chamber. The method also includes steps of aerosolizing a sterilant to create an aerosolized sterilant and delivering the aerosolized sterilant to the sterilization chamber through a sterilant outlet disposed within or at a boundary of the sterilization chamber, wherein the sterilant is substantially prevented from mixing with ozone prior to delivery of the aerosolized sterilant to the sterilization chamber. The method also includes a step of delivering ozone to the sterilization chamber through an ozone outlet disposed within or at the boundary of the sterilization chamber while the aerosolized sterilant is present in the sterilization chamber, whereby an oxidative aerosol sterilant is created within the sterilization chamber by mixing of the aerosolized sterilant and the ozone. The aerosolized sterilant and the ozone to the sterilization chamber is continued to be delivered for a sterilizing-effective period of time, whereby a desired assurance of sterility of the object to be sterilized is achieved.

Delivering ozone to the sterilization chamber may include delivering ozone through a plurality of ozone outlets disposed within or at the boundary of the sterilization chamber. Delivering the aerosolized sterilant to the sterilization chamber may include delivering the aerosolized sterilant through a plurality of sterilant outlets disposed within or at the boundary of the sterilization chamber. The plurality of sterilant outlets and the plurality of ozone outlets may be interspersed to facilitate mixing of the sterilant and the ozone within the sterilization chamber. At least a portion of the plurality of sterilant outlets and at least a portion of the plurality of ozone outlets may be incorporated into or form a pin mat disposed within the internal volume of the sterilization chamber, the pin mat being adapted to support the object to be sterilized in the portable sterilization device.

The sterilant used in the method may include one or more sterilants, including hydrogen peroxide.

The ozone delivered to the chamber in the method may be generated from air drawn from the sterilization chamber through an air return opening disposed in the sterilization chamber, such that an airflow circulation is established by air withdrawn from the sterilization chamber being used to generate ozone, which is then introduced back to the sterilization chamber through the ozone outlet.

According to additional implementations of the disclosure, a sterilization method utilizes a portable sterilization device according to implementations of the disclosure discussed herein. The method includes steps of providing a sterilant to a sterilant delivery device of the portable sterilization device, placing an object to be sterilized within a sealable sterilization chamber of the portable sterilization device, and sealing the sterilization chamber. The method further includes a step of activating the portable sterilization device, whereby the sterilant is aerosolized and delivered to the sterilization chamber through a sterilant outlet disposed within the sterilization chamber without exposing the sterilant to ozone prior to delivery of the sterilant through the sterilant outlet while simultaneously delivering ozone to the sterilization chamber through an ozone outlet disposed within the chamber, such that an oxidative aerosol sterilant is created within the sterilization chamber by mixing of the aerosolized sterilant and the ozone. The delivery and mixing of aerosolized sterilant and ozone continues for a period of time sufficient to achieve a desired level of sterility of the object within the chamber. For example, the period of time may be sufficient to obtain a sterility assurance level (SAL) of $10^{-6}$ for inactivation of a 6 log population of organisms determined to be most resistant organisms (MRO) to sterilization.

The sterilant used in the method may include one or more sterilants including hydrogen peroxide.

The ozone delivered to the chamber in the method may be generated from air drawn from the sterilization chamber through an air return opening disposed in the sterilization chamber, such that an airflow circulation is established by air withdrawn from the sterilization chamber being used to generate ozone, which is then introduced back to the sterilization chamber through the ozone outlet.

In some versions of the method, the sterilant delivery device is in fluid communication with a plurality of sterilant outlets disposed in the sterilization chamber, such that aerosolized sterilant is simultaneously delivered to multiple locations within the sterilization chamber. Similarly, there may be a plurality of ozone outlets connected by a manifold to the ozone source, such that ozone is simultaneously delivered to multiple locations within the sterilization chamber. Additionally, there may be a plurality of air return openings, and the air return openings may be placed within the sterilization chamber such that a desired air flow and/or mixing of the aerosolized sterilant and ozone is achieved within the sterilization chamber, to ensure a desired sterility assurance level of all areas of any object or objects within the sterilization chamber. Where there are a plurality of sterilant outlets and a plurality of ozone outlets, the sterilant outlets and the ozone outlets may be interspersed to a variety of degrees to further facilitate mixing of the aerosolized sterilant and the ozone. In some instances, the sterilant outlets and/or the ozone outlets may be incorporated into or form a pin mat within the sterilization chamber, the pin mat being adapted to support the object or objects being sterilized.

Upon initiation of a sterilization method, when the sterilization chamber is sealed, the sterilization chamber will contain the object(s) to be sterilized as well as some ambient air. As the process starts, some of that ambient air may be evacuated, leaving the object(s) to be sterilized and remaining ambient air at some level of vacuum. As the aerosolized sterilant and ozone are dispensed or delivered to the sterilization chamber, the sterilization chamber will include the object(s) to be sterilized, gases including ozone, water (humidity) and gaseous byproducts of the reaction of sterilant and ozone, aerosolized sterilant and oxidative aerosol sterilant, aerosolized water, and liquid water that may have condensed on the sterilization chamber wall(s) and/or the objects to be sterilized. Discussion herein relating to the removal or withdrawal of "air" or "fluid" from the sterilization chamber, including through an "air return," and "air return inlet," or an "air return opening" is intended to embrace the passage of any fluid that may at the applicable time be within the sterilization chamber, including the original ambient air (gaseous) and gases containing ozone and/or aerosolized liquid components. Where such fluid is to be reused to supply an ozone generator, the fluid may be treated appropriately to maximize the efficiency of the ozone generator, including by filtering and/or drying the fluid/air before supplying it to the ozone generator.

The terms "determine," "calculate," and "compute," and variations thereof, as used herein, are used interchangeably and include any type of methodology, process, mathematical operation or technique.

It is to be noted that the term "a" or "an" entity refers to one or more of that entity. As such, the terms "a" (or "an"), "one or more" and "at least one" can be used interchangeably herein. It is also to be noted that the terms "comprising," "including," and "having" can be used interchangeably.

Unless otherwise specified, any use of any form of the terms "connect," "engage," "couple," "attach," or any other term describing an interaction between elements is not meant to limit the interaction to direct interaction between the elements and may also include indirect interaction between the elements described. In the following discussion and in the claims, the terms "including" and "comprising" are used in an open-ended fashion, and thus should be interpreted to mean "including, but not limited to . . . " The various characteristics mentioned above, as well as other features and characteristics described in more detail herein will be readily apparent to those skilled in the art with the aid of the present disclosure upon reading the following detailed description of the embodiments.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "means" as used herein shall be given its broadest possible interpretation in accordance with 35 U.S.C. § 112(f). Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

It should be understood that every maximum numerical limitation given throughout this disclosure is deemed to include each and every lower numerical limitation as an alternative; as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION OF THE INVENTION

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

Embodiments of the present disclosure generally relate to devices and methods for sterilizing medical equipment. In particular, the present disclosure provides portable devices for sterilizing surgical equipment in emergency medical situations, including in remote locations where modern sterilization equipment is not available. For example, emergency medical personnel such as combat medics can benefit from the various advantages of the devices and methods of the present invention, which include features such as process automation and feedback, safety features, an intuitive control interface, process reliability, minimal power requirements, and battery-powered operation. Embodiments of the present disclosure can be referred to as a rugged ozone sterilization system (ROSS) and are configured to meet a critical need for sterilization in portable hospitals, initial treatment and assessment areas, field units and establishments that lack sterilization or disinfection infrastructure. In some embodiments, devices of the present disclosure sterilize surgical instruments quickly at ambient temperature, under battery power, or available AC, using a pre-measured packet of hydrogen peroxide and on-board generated ozone from air within the device (e.g., a portion of ambient air remaining in the device after sealing the device and initiating a sterilization operation).

In an example aspect, devices of the present disclosure solve the problem of sterilization of surgical instruments or medical equipment in remote locations or areas, for example areas following natural disasters such as an earthquake, hurricane, flood or tsunami, or in war-torn regions for use by medics or field hospitals. In an example aspect, devices of the present disclosure are useful as low-temperature terminal sterilization of medical devices, dental and veterinary device sterilization, and disinfection generally. Advantageously, the device includes process automation and feedback, safety features, an intuitive control interface, process reliability, minimal power requirements, and battery-powered operation to benefit the user. In an example aspect, devices of the present disclosure increase the availability of sterile surgical instruments due to its highly portable, rugged design and quick process times thus allowing healthcare personnel to continue to treat the critically injured and improve the survival rate of the wounded in Forward Operating Bases and areas of need worldwide.

Figure 1A:
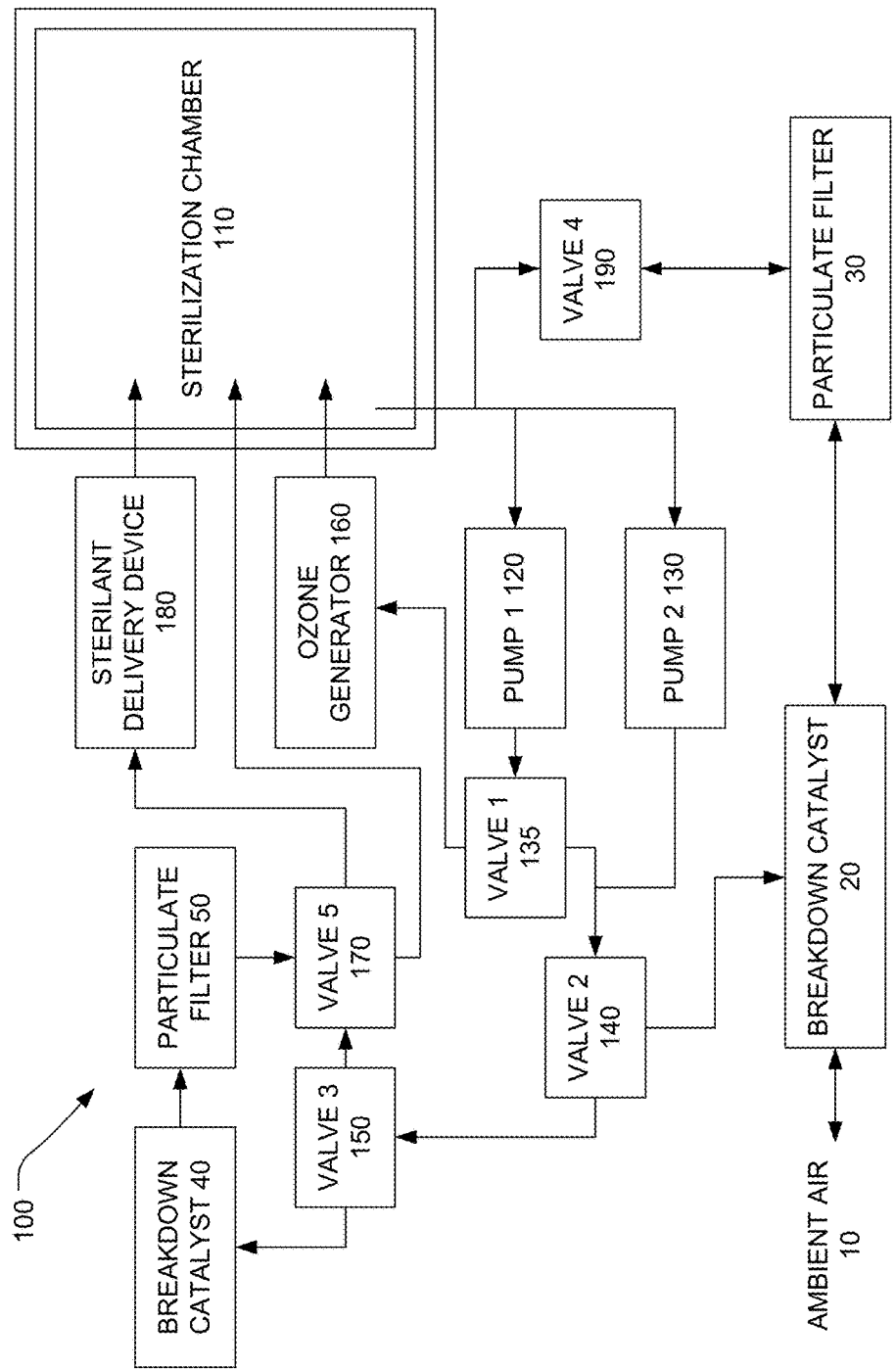
FIG. 1A is a representative illustration of a block flow diagram according to one aspect of the invention.
Figure 3:
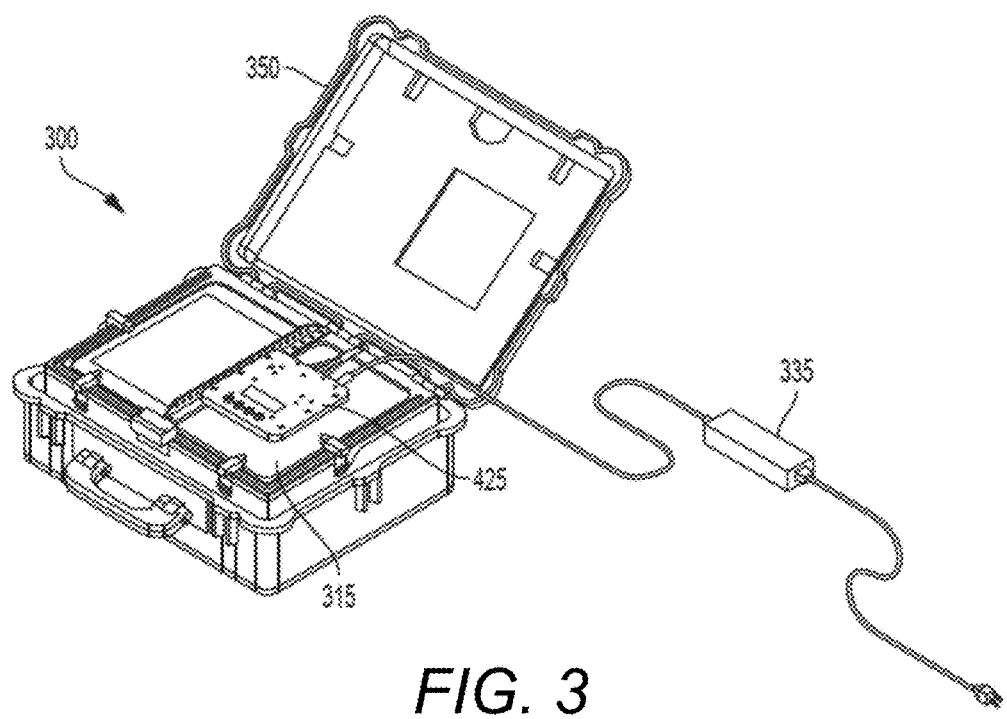
FIG. 3 is a representative illustration of a sterilization top for a sterilization device according to an example aspect.

As illustrated in the flow diagram of FIG. 1A, embodiments of the present disclosure include sterilization device 100. In an example aspect, sterilization device 100 is evacuated in order to reach operational vacuum. The vacuum need not be a strong vacuum, but may be a mild vacuum of 500-700 Torr. In other words, sterilization device 100 operates at a vacuum relative to ambient pressure. The relative vacuum is maintained beyond a specified threshold during the cycle; the threshold is useful as a method of leak detection. A feedback display (as shown on sterilization top of FIG. 3) will indicate if vacuum is insufficient for sterilization to be successful. In an example aspect, sterilization chamber 110 includes a base sealingly engaged to a top via a seal or an o-ring. The time required for evacuation is relatively short, i.e. about 30 seconds.

Remaining air within sterilization device 100 is useful in the operation of the device. Air from sterilization chamber 110 is directed through pumps 120 and/or 130 and through valve 135 and valve 140, upon which valve 140 is closed to prevent leaks to ambient air 10. The air flow is then directed to ozone generator 160 via valve 135 to provide air containing ozone, which is introduced into the sterilization chamber 110 via an ozone outlet. Ozone generator 160 is also referred to interchangeably herein as ozone delivery device.

In the prior utility application incorporated by reference herein (the "prior application"), the air containing ozone was fed to a sterilant delivery device (e.g., a compressive nebulizer) and was used by the sterilant delivery device to simultaneously mix and aerosolize with a dilute liquid sterilant, thereby creating an aerosolized oxidative sterilant. The aerosolized oxidative sterilant products (discussed in more detail below), however, are very reactive and have a very short active life. Because the ozone and sterilant were mixed in the sterilant delivery device to create the aerosolized oxidative sterilant while still in the sterilant delivery device, the aerosolized oxidative sterilant delivered to the sterilization chamber by the prior device was not as strong or effective as possible, reducing efficiency of the prior sterilization device.

Figure 1B:
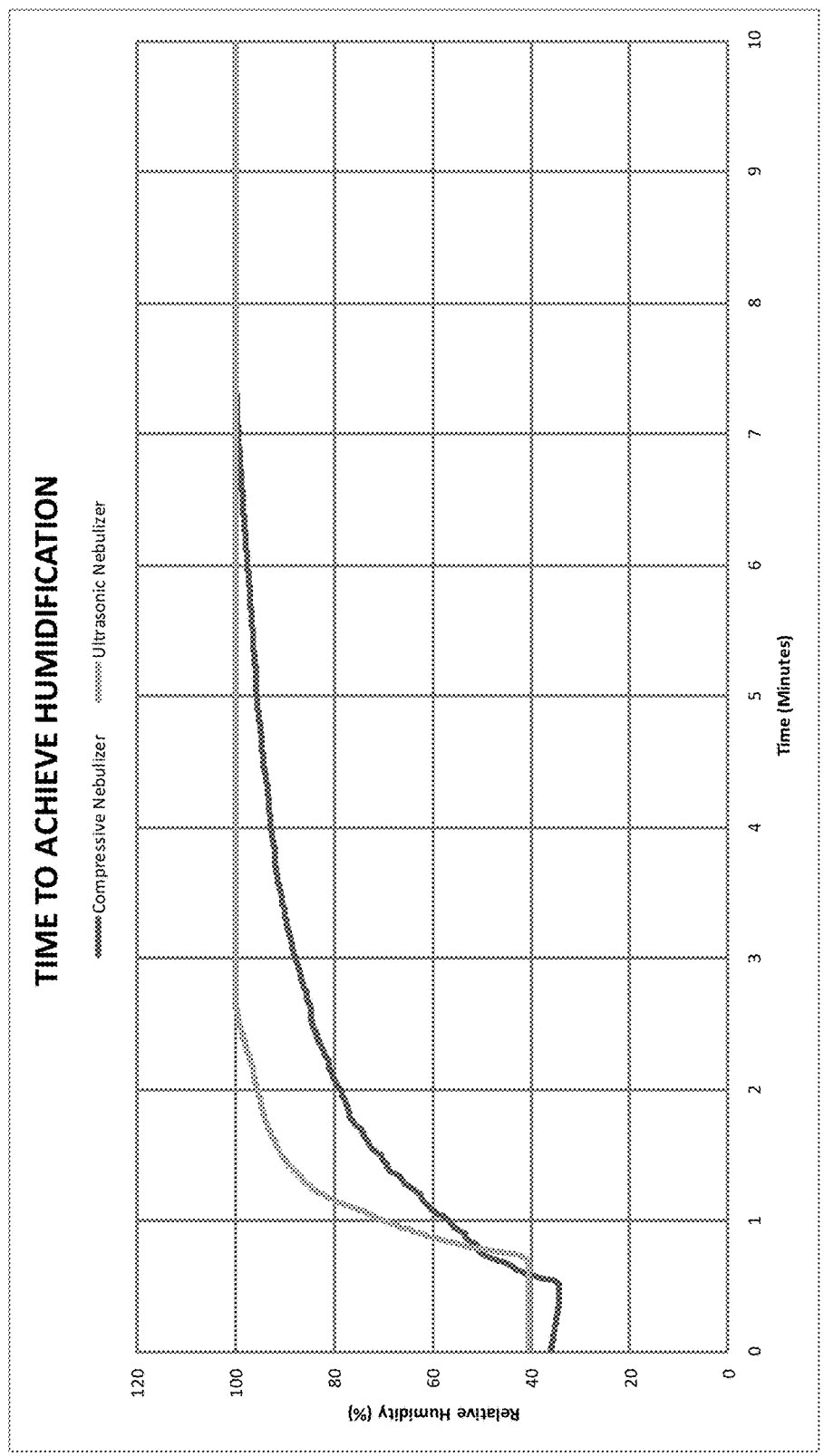
FIG. 1B is a chart illustrating the speed at which 100% humidity is achieved within a representative sterilization chamber utilizing a representative ultrasonic nebulizer as opposed to using a representative compressive nebulizer.

To address this issue, some embodiments of the present disclosure separately deliver aerosolized sterilant and ozone to the sterilization chamber 110, and air with ozone is not used to operate sterilant delivery device 180. Instead, air not containing ozone may be fed to sterilant delivery device 180, which may be a nebulizer, if air flow is required for sterilant delivery device 180 to function, through a nebulizer feed line that is connected to valve 170. If air flow is not necessary for sterilant delivery device 180 to deliver aerosolized sterilant to the sterilization chamber 110, then the air flow from valve 170 to sterilant delivery device 180 may be omitted, as illustrated in FIG. 1D, or only operated as necessary. Separately, as discussed above, air is delivered to ozone generator 160, and the output of ozone generator 160 is directly fed to sterilization chamber 110 without first passing through sterilant delivery device. In an example aspect, the air containing ozone, also referred to as plasma gas sterilant interchangeably herein, only mixes with the aerosolized sterilant to form the aerosolized oxidative sterilant within the interior volume of the sterilization chamber 110 itself. Accordingly, the sterilant is prevented from mixing with ozone prior to being dispersed through the sterilant outlet into the sterilization chamber 110. Breakdown catalyst 40 may be used to ensure that ozone is not present (or is present only in small enough amounts to be negligible) in any air delivered to sterilant delivery device 180.

In an example aspect, sterilant delivery device 180 is or includes a nebulizer. In an example aspect, sterilant delivery device 180 includes an aerosolizing component such as an ultrasonic nebulizer, a piezoelectric nebulizer, a mechanical nebulizer, a compressive nebulizer, a misting nozzle supplied by a pump, a misting nozzle supplied by a linear actuator, an ultrasonic spray nozzle, an air atomizing nozzle, a Venturi nozzle, a microfluidic pin orifice, a heat vaporizer, or a diesel fuel injector. The sterilant delivery device 180 serves not only to aerosolize sterilant and to deliver the sterilant to the sterilization chamber 110, but also serves to humidify the gas or air within the sterilization chamber 110, as the sterilant is often a dilute solution of sterilant and water, as discussed in more detail below. Humidifying the gas or air within the sterilization chamber 110 may aid in the reactions within the chamber that result in the production of the oxidative aerosol sterilant and/or in the reactions of the oxidative aerosol sterilant with the organisms on the equipment being sterilized. Accordingly, it can be an advantage to increase the speed at which the gas or air within the sterilization chamber 110 is humidified, thereby reducing the time for a desired sterilization assurance. While embodiments of the disclosure of the prior application discussed use of a compressive nebulizer, it has been found that use of an ultrasonic nebulizer results in achieving 100% humidity within the sterilization chamber 110 at a faster rate, as illustrated by FIG. 1B. Accordingly, while embodiments of the present disclosure embrace a variety of aerosolizing components or nebulizing elements, certain embodiments embrace the use of aerosolizing components or nebulizing elements that achieve high humidity more quickly, such as using an ultrasonic nebulizer.

The nebulizer or other aerosolizing component is preloaded or filled with a liquid sterilant. In an example aspect, the liquid sterilant is contained in a nebulizer reservoir. In an example aspect, the liquid sterilant is hydrogen peroxide ($H_2O_2$). In an example aspect, the liquid sterilant is a 7% hydrogen peroxide solution. Sterilant concentrations are increased to an effective threshold level during the simultaneous but separate injection of liquid sterilant such as hydrogen peroxide solution and of air containing ozone. In an example aspect, sterilant delivery device 180 delivers or injects an aerosolized sterilant directly to sterilization chamber 110, where it mixes with the air containing ozone to form the aerosolized oxidative sterilant. In an example aspect, the aerosolized oxidative sterilant includes a simultaneously mixed combination of air containing ozone mixed with sterilant such as hydrogen peroxide solution. The time required for sterilant injection is about 7 minutes in some example aspects, and such time may be further improved upon utilizing additional example aspects discussed herein. Assurances are in place to indicate the unlikely event of a nebulizer or other nebulizing feature or aerosolizing component failure. In one example aspect, a backpressure in the nebulizer feed line is available under "Process Info" of the feedback display. If pressure falls below threshold backpressure level of 2 PSI, then the system aborts, initiates breakdown, and gives indication of nebulizer failure. In other example aspects, other relevant component statuses may be monitored using one or more sensors and/or feedback loops, as may be known in the art to detect and notify of sterilant delivery failure.

After a successful sterilant injection phase to achieve sterilant concentration above effective threshold level taking about 3 minutes, sterilant delivery device 180 continuously delivers an effective concentration of the aerosolized sterilant to sterilization chamber 110, for about 21.6 minutes (or other effective time, as may be improved upon utilizing any combination of the example aspects disclosed herein, including combinations not specifically disclosed herein), to expose the contents (i.e. bare surgical instruments, surgical instruments within packaging, and surgical instruments within sterile storage containers) to the effective concentration thus performing sterilization of the contents.

After successful completion of sterilant exposure to the contents, a breakdown process is initiated in order to prepare the system for being unsealed and for the contents to be safely removed, wherein the acceptable ozone concentration upon completion is 0.1 ppmv. During the breakdown operation, air from within the device is diverted through valve 150 to breakdown catalyst 40. Upon completion of the breakdown operation, which requires about 12 minutes, the feedback display will indicate sterilization is complete and indicate that the device may be opened for removal of the contents. A 30-minute timer automatically initiates and the load remains sterile until the user, prompted by the feedback display, presses 'yes' to open. Although thirty minute sterility duration is validated in an example aspect, extended sterility durations are contemplated. This gives the user flexibility to have the sterile instruments available at the needed time. In an example aspect, the system is not vented until initiated by the user. To vent, air is drawn through breakdown catalyst 20 and particulate filter 30, which may be a 5 micrometer filter, through valve 190. The time required for venting is relatively short, i.e. about 30 seconds.

In an example aspect, surgical instruments can be placed in the device, and after a predetermined process time the device can be opened and the surgical tools are ready for immediate use. Advantageously, the tools are already at ambient temperature. In an example aspect, the sterilization device is configured to have a process time of less than one hour. In other embodiments, the process time may be less than forty-five minutes. In yet another embodiment, the process time is between about twenty minutes and about forty minutes. In an example aspect, the total time for the sterilization device to sterilize the contents is about thirty-six minutes.

As those skilled in the art will appreciate, the time values set forth in the foregoing paragraphs may vary depending upon a variety of parameters, including equipment performance and capacity.

Figure 1C:
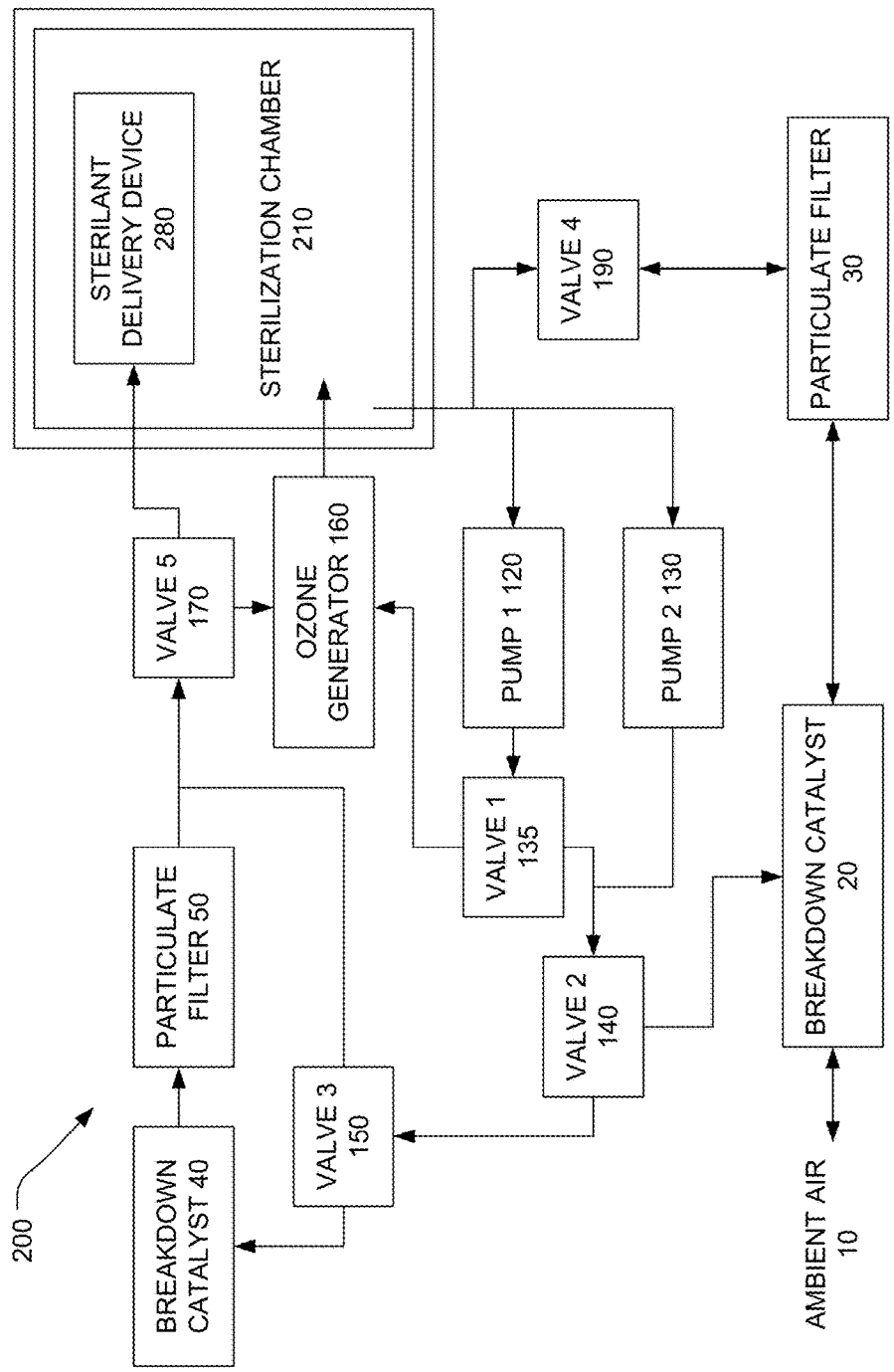
FIG. 1C is a representative illustration of a block flow diagram according to another aspect of the invention.
Figure 1D:
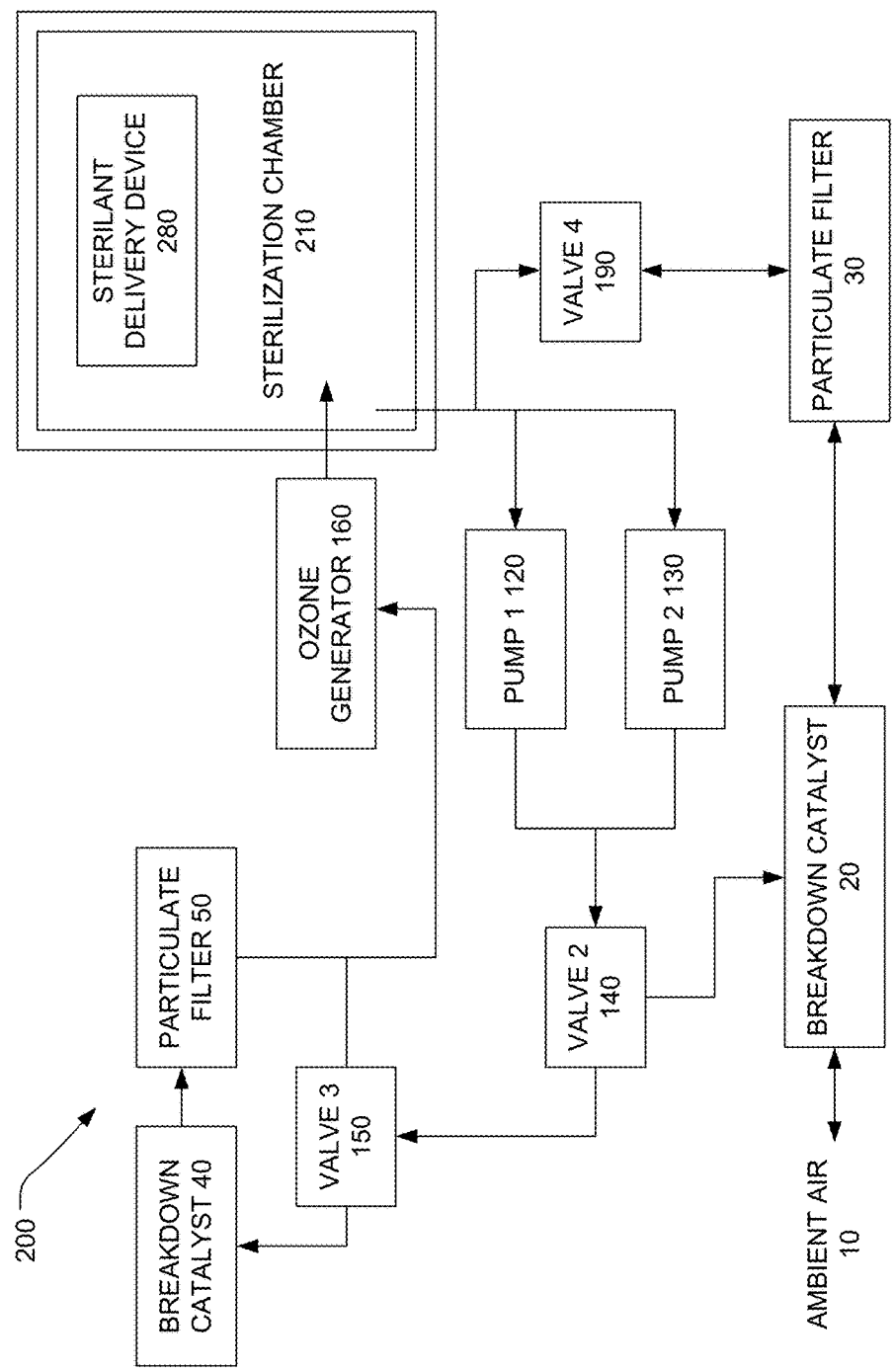
FIG. 1D is a representative illustration of a block flow diagram according to another aspect of the invention.

As illustrated in the flow diagram of FIG. 1C, embodiments of the present disclosure include a sterilization device 200 similar to device 100, except that sterilant delivery device 280 is located within sterilization chamber 210. In an example aspect, sterilant delivery device 280 is or includes a nebulizer. In an example aspect, sterilant delivery device 280 includes an aerosolizing component such as an ultrasonic nebulizer, a piezoelectric nebulizer, a mechanical nebulizer, a compressive nebulizer, a misting nozzle supplied by a pump, a misting nozzle supplied by a linear actuator, an ultrasonic spray nozzle, a Venturi nozzle, a microfluidic pin orifice, an air atomizing nozzle, a heat vaporizer, or a diesel fuel injector. The nebulizer or other aerosolizing component is preloaded or filled with a liquid sterilant. The liquid sterilant is contained in a nebulizer reservoir. In an example aspect, the sterilant is hydrogen peroxide ($H_2O_2$). In an example aspect, the sterilant is a 7% hydrogen peroxide solution.

Figure 1E:
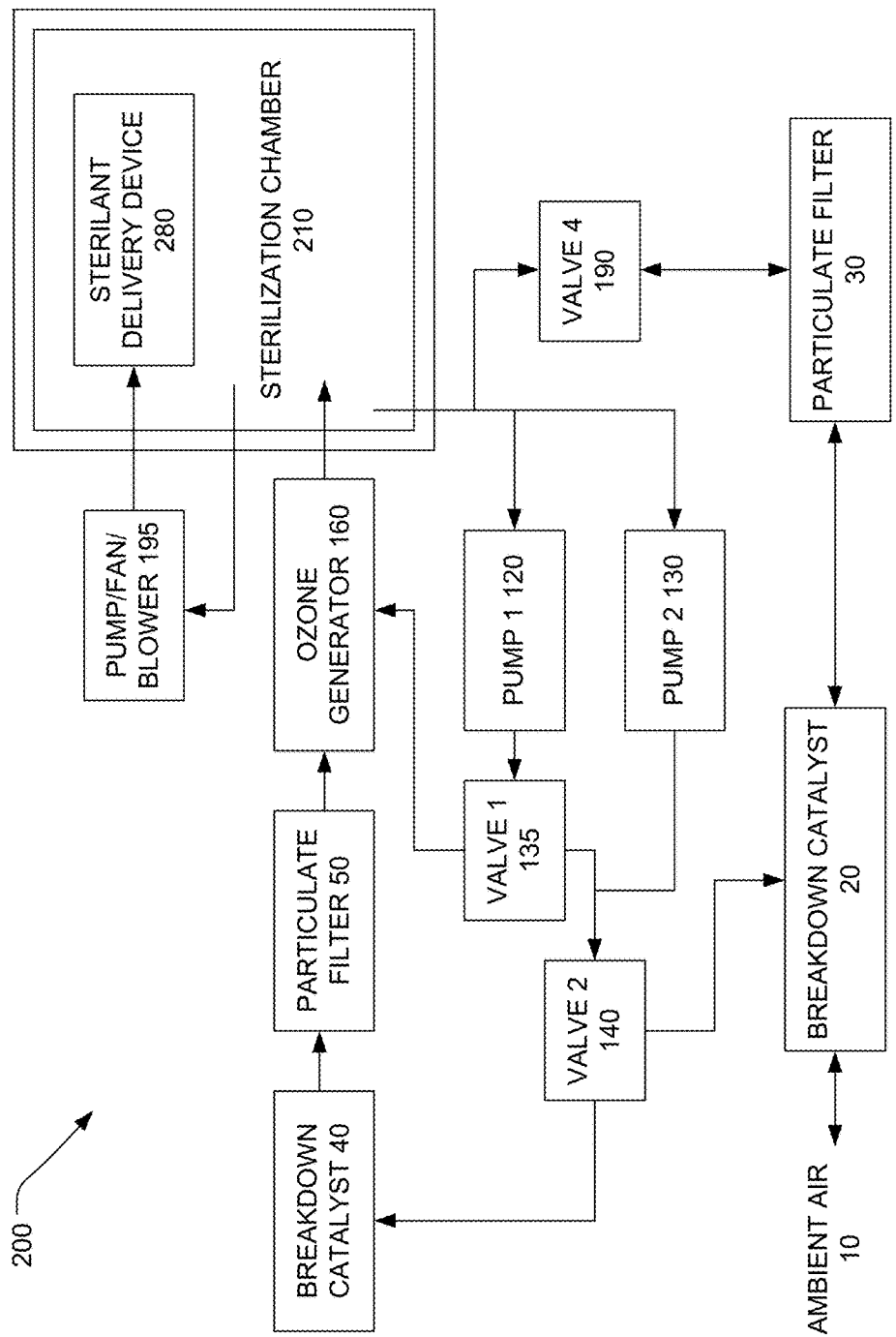
FIG. 1E is a representative illustration of a block flow diagram according to another aspect of the invention.
Figure 1F:
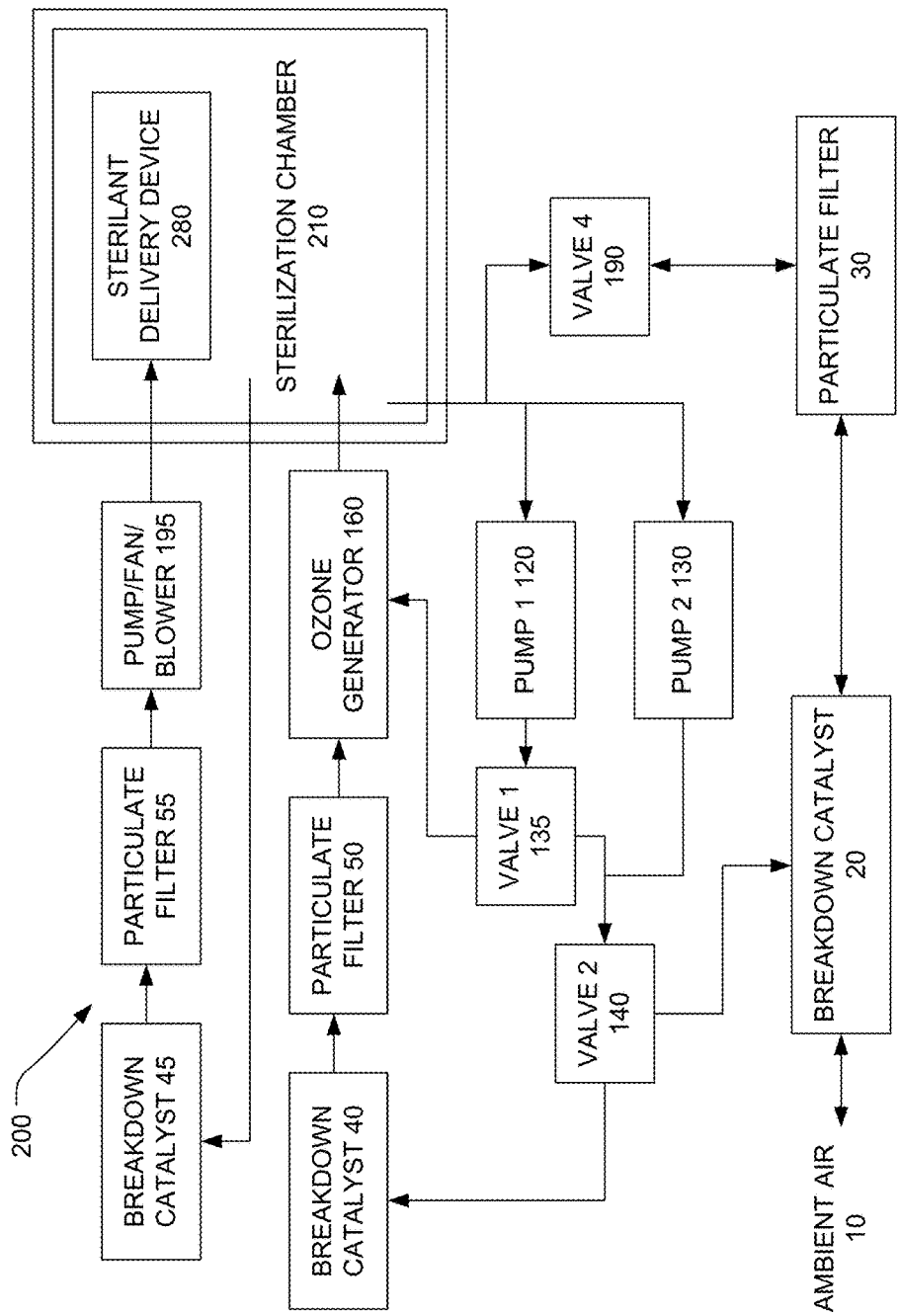
FIG. 1F is a representative illustration of a block flow diagram according to another aspect of the invention.

FIGS. 1D-1F illustrate alternate embodiments of the sterilization device 200 of the present disclosure, illustrating alternate methods for operating sterilant delivery device 280. Although not specifically illustrated in alternate figures, embodiments of the sterilization device 100 of FIG. 1A (in which the sterilant delivery device 180 is not located within the sterilization chamber 110) may be varied along the lines illustrated in FIGS. 1D-1F similarly. In the sterilization device of FIG. 1C, the ozone generator 160 may be supplied with air directly from the sterilization chamber 210 using valve 135, or may be supplied with air that has been filtered by particulate filter 50 using valve 170.

In the example aspect of the sterilization device 200 of FIG. 1D, the ozone generator may be similarly supplied with air directly from the sterilization chamber using valve 135, or may be supplied with air that has been filtered by particulate filter 50. The sterilization device 200 of FIG. 1D also differs from the example aspect of FIG. 1C in that the sterilant delivery device 280 of this example is a device that does not require a separate airflow to provide aerosolized sterilant to the sterilization chamber 210. For example, the sterilant delivery device 280 of this example may be an ultrasonic nebulizer. As another example, the sterilant delivery device 280 may include or incorporate a fan or blower (not separately shown) that passes sufficient air from the sterilization chamber 210 through the sterilant delivery device 280 to provide aerosolized sterilant to the sterilization chamber. While such an arrangement may result in a small amount of ozone passing through the sterilant delivery device 280, the amount of ozone will be relatively small as opposed to using output of the ozone generator 160 to supply the sterilant delivery device 280 as in the prior application.

FIGS. 1E and 1F illustrate further example aspects of the sterilization device 200 in which the sterilant delivery device 280 is supplied with air drawn from the sterilization chamber 210 in a separate supply loop from that used with the ozone generator 160. In the example aspect of FIG. 1E, the sterilant delivery device 280 is supplied with air from the sterilization chamber 210 using a pump, fan or blower 195 that is external to the sterilization chamber. As mentioned above, while such an arrangement may supply a small amount of ozone to the sterilant delivery device 280, the amount of ozone will be relatively small as opposed to using output of the ozone generator 160 to supply the sterilant delivery device 280. If further ozone reduction is desired, the example aspect of FIG. 1F may be used, in which air drawn from the sterilization chamber 210 is first passed through a breakdown catalyst 45 and optionally a particulate filter 55. While the pump, fan, or blower 195 is shown as being downstream from the breakdown catalyst 45 and particulate filter 55 in this illustration, it should be understood that the pump, fan, or blower 195 may be located upstream of either or both of these components.

Figure 4:
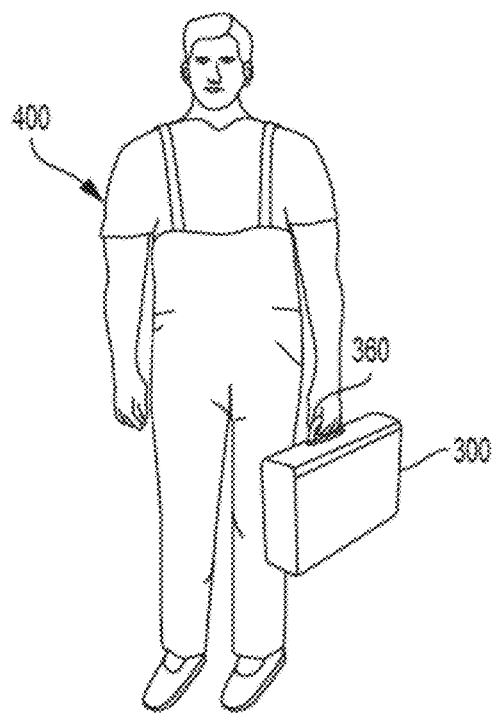
FIG. 4 is a representative illustration of a person carrying a portable sterilization device according to an example aspect.

In an example aspect, the sterilization device is portable, having a size and weight (e.g., a maximum weight of seventy pounds) to permit carrying of the device by a single person, as illustrated in FIG. 4. Sterilization device is interchangeably herein referred to as portable sterilization device. In an example aspect, the portable sterilization device comprises an external housing unit, a sealable sterilization chamber (110, 210) located within the external housing unit, and a sterilant delivery device (180, 280) operatively associated with the sterilization chamber. In an example aspect, the sterilant delivery device further comprises a nebulization element or aerosolizing component and one or more sterilants, wherein the nebulization element or aerosolizing component is configured to convert the one or more sterilants into an aerosolized sterilant and deliver the aerosolized sterilant into the sterilization chamber, where it mixes with ozone provided by the ozone generator 160 to form the oxidative aerosolized sterilant. In an example aspect, the portable sterilization device further comprises an ozone delivery device or ozone generator (160) operatively associated with the sterilization chamber (110, 210). In an example aspect, the ozone delivery device is configured to deliver ozone into the sterilization chamber (110, 210). In an example aspect, the portable sterilization device further comprises an airflow circulation assembly. In an example aspect, the airflow circulation assembly includes one or more pumps (120, 130), one or more valves (140, 150, 170, 190), inlets, outlets, and tubing connecting the one or more pumps and valves. In an example aspect, the portable sterilization device further comprises a control panel configured to operate the sterilization chamber, the sterilant delivery device, the ozone delivery device, and the airflow circulation assembly. In an example aspect, the portable sterilization device further comprises a power source operatively associated with the control panel and configured to supply power to the sterilization chamber, the sterilant delivery device, the ozone delivery device, and the airflow circulation assembly; whereupon activation, the control panel is configured to execute an operation to provide simultaneous delivery of the aerosolized sterilant and the ozone into the sterilization chamber where it mixes to form the oxidative aerosolized sterilant.

Figure 2A:
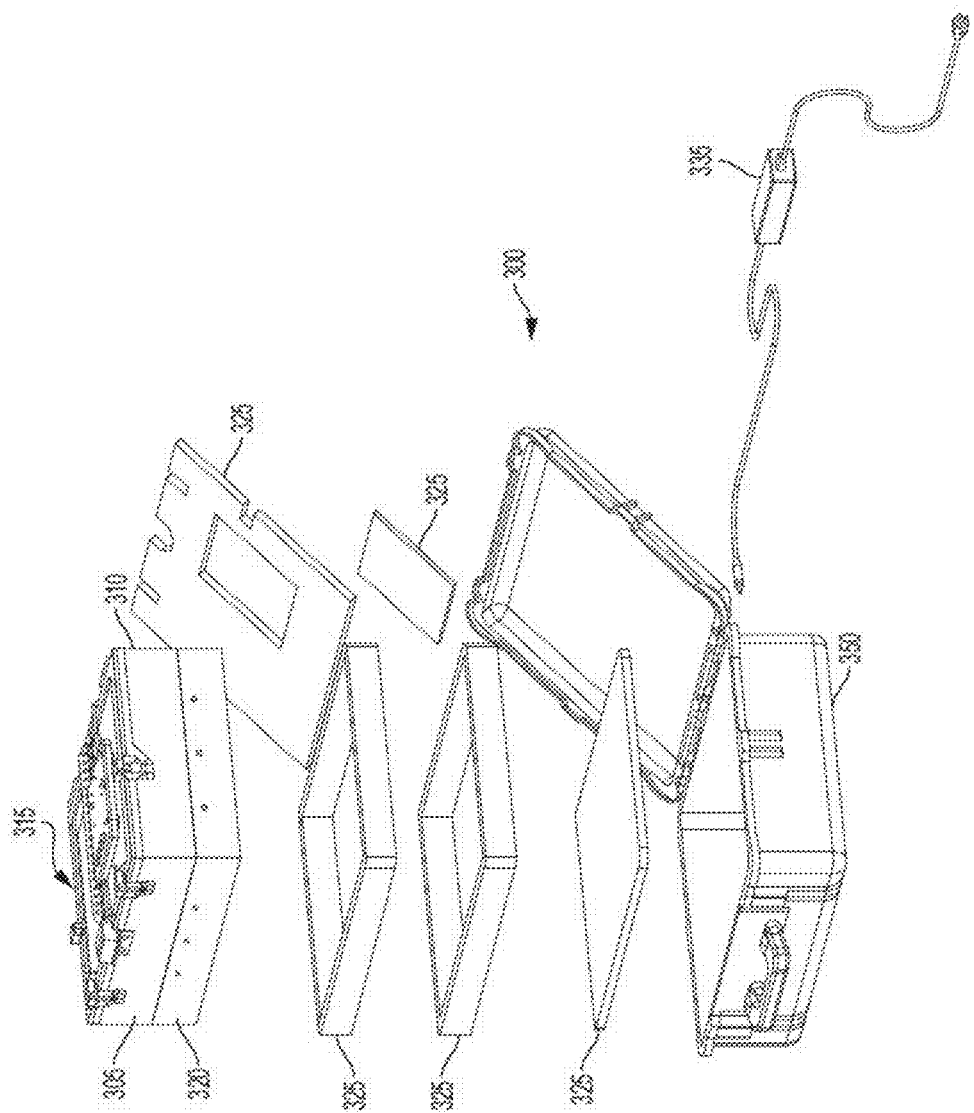
FIG. 2A is a representative illustration exploded view of a sterilization device according to an example aspect.

FIG. 2A is a representative illustration exploded view of an exemplary sterilization device according to an example aspect. Sterilization device 300 includes housing 350, foam supports 325, assembly of chambers 305, and power adapter 335. Assembly of chambers 305 includes sterilization chamber 310 having top 315 and components chamber assembly 320. As illustrated in FIG. 2B, and according to an example aspect, sterilization device 300 includes case 350. Case 350 is referred to interchangeably herein as external housing or housing. Case 350 is made of any sturdy light weight material or plastic as known in the art, for example, an injection molded impact resistant co-polymer. In an example aspect, case 350 includes an anodized aluminum frame. In an example aspect, case 350 is an external dust proof and water resistant case with no components penetrating or external to the shell. In an example aspect, case 350 is IP67 certified.

Case 350 includes an interior lined with closed cell polyethylene foam support 325, such as foam support sold under the trademark ETHICON®, a trademark owned by the Johnson and Johnson Corporation. Foam support 325 surrounds sterilization chamber 310. There is adequate spacing between the interior of case 350 and sterilization chamber 310 to include foam support and an optional gap. Case 350 includes a top and a bottom and a closing mechanism. Case 350 includes latches hinges, a locking mechanism, or both. Latches hinges 340 are made of a corrosion-resistant material, for example, stainless steel. The locking mechanism may be an electromagnetic locking mechanism or other such mechanism as known in the art. Case 350 also includes handle 360 for ease in portability. Advantageously, device 300 is portable (e.g., weights no more than seventy pounds and has a size and shape permitting a single individual to carry it, as illustrated in FIG. 4) and everything needed for producing sterilant is self-contained. A clean water source is not required and only minimal power requirements are needed in the operation of the sterilization device, thus further enhancing the portability of the device.

In an example aspect, the portable sterilization device includes a sterilization chamber configured to accept a plurality of medical instruments. In an example aspect, the portable sterilization device includes a sterilization chamber configured to accept a plurality of medical instruments wherein the simultaneous delivery of the aerosolized sterilant and the ozone into the sterilization chamber containing the plurality of medical instruments at a pre-determined ozone concentration for a pre-determined time period is sufficient to obtain a sterility assurance level (SAL) of 10-6 for inactivation of a 6 log population of organisms determined to be most resistant organisms (MRO) to sterilization. In an example aspect, the one or more sterilants comprise hydrogen peroxide.

As illustrated in FIG. 2C, and according to an example aspect, sterilization device 300 includes sterilization chamber 310. In an example aspect, sterilization chamber 310 is hermetically welded within case 350. In an example aspect, sterilization chamber 310 includes latches hinges, a locking mechanism, or both. Sterilization chamber 310 includes mat 330 to line the interior bottom, which as discussed in more detail below, may be a pin mat. Sterilization chamber 310 is configured for receiving surgical instruments 370, or other items or objects, to be sterilized. In an example aspect, surgical instruments 370 are placed upon mat 330, which is silicone or other suitable material. In one embodiment, sterilization is accomplished by an oxidation process facilitated by a sterilant. Advantageously, instruments 370 are exposed to a sterilization process that is non-toxic and does not require high temperatures to inactivate contaminant microorganisms. The sterilization chamber will be described in further detail below including the sterilant delivery device and associated sterilant outlets, and the ozone delivery device and associated ozone outlets as shown in FIGS. 9-18.

In an example aspect, a sterilization chamber for sterilizing a plurality of medical instruments is provided. In an example aspect, the sterilization chamber comprises an instrument receptacle comprising a sealing mechanism; at least one ozone inlet; at least one airflow outlet; and a sterilant delivery device comprising a nebulization element or aerosolizing component and one or more sterilants, wherein the nebulization element or aerosolizing component is configured to aerosolize the sterilant and deliver the aerosolized sterilant into the instrument receptacle before any mixing with ozone occurs, such that mixing of the aerosolized sterilant and ozone first occurs in the sterilization chamber to form the oxidative aerosolized sterilant or oxidative aerosol sterilant. In an example aspect, the one or more sterilants comprise hydrogen peroxide.

As illustrated in FIG. 3, sterilization device 300 according to an example aspect includes sterilization top 315. In an example aspect, sterilization top 315 includes output 425 for process feedback and control, error reporting, or other operational messages. Output 425 is also referred to interchangeably herein as control panel or feedback display 425. In an example aspect, the sterilization device further comprises one or more sensors operatively associated with the control panel and configured to monitor one or more operational parameters of the device. In an example aspect, the one or more operational parameters comprise one or more of closure integrity, sterilant levels, ozone levels, airflow velocity, air pressure, valve operation, temperature, humidity, power levels, electrical current, device operation, sterilization cycle lengths, and sterilization cycle number.

In an example aspect, output 425 is an OLED screen, where OLED stands for organic light-emitting diode. Sterilization device 300 may also include inputs such as a keyboard, momentary switches, or a microphone to receive inputs, commands, parameters, etc. and provide operation controls based on such inputs. In an example aspect, sterilization device 300 is configured to request and process inputs and outputs using a software control package. In an example aspect, the software control package is configured to communicate with sensors and use sensor inputs to facilitate a desired operation of the device. In another example aspect, sterilization device 300 is configured to request and process inputs and outputs using an application for a device such as a smart phone or tablet, for example. In an example aspect, an input may include activation of the sterilant breakdown routine entered by a user. In an example aspect, sterilization device 300 includes a software control package configured to automatically trigger the sterilant breakdown routine during the process of operation and in response to any device failures, for example, to abort. The software package optionally includes parameter monitoring and process data storage and record retention and output. It will be appreciated by those of skill in the art that the automation, operation, and/or control of the device may be accomplished by software, hardware, firmware, or a combination thereof. For purposes of the description, the term "software" is interchangeable with hardware, firmware or combinations of software, hardware or firmware.

In an example aspect, the sterilization device or the sterilization chamber or both are optionally configured with controls such as locking mechanisms to prevent opening the device while operating, thereby breaking the seal and causing failure of the sterilization process. In an example aspect, locking controls are configured to require a full sterilant breakdown routine prior to allowing the opening of the case or allowing the release of a vacuum which may be built up within the case. In one embodiment, an operational vacuum acts as a method of leak detection and as a safety provision. In an example aspect, device 300 includes a leak detector to detect leaking from outside the device to inside or vice versa.

As illustrated in FIG. 4, sterilization device 300 is configured to be carried by a person, represented by FIG. 400. FIG. 400 can transport the sterilization device easily using handle 360 to wherever the contents, once sterilized, are needed and used. In an example aspect, sterilization device 300 is light weight. In an example aspect, sterilization device 300 is at most seventy pounds. In another example aspect, sterilization device 300 is less than fifty pounds. In another example aspect, sterilization device 300 is between about twenty pounds and about fifty-five pounds. In yet another example aspect, sterilization device 300 is about thirty-eight pounds. As one skilled in the art would appreciate, alternative lighter weight materials or components may be used to make the sterilization device lighter. In an example aspect, the sterilization device is at most forty pounds. In another example aspect, the sterilization device is at most thirty pounds. In yet another example aspect, the sterilization device is at most twenty pounds. In other example aspects, the sterilization device is limited in weight and or size/dimensions to comply with one or more OSHA weight requirements for portability by a single person and/or transportation carrier (e.g., airline) weight requirements for checked and/or carry-on luggage.

Figure 5:
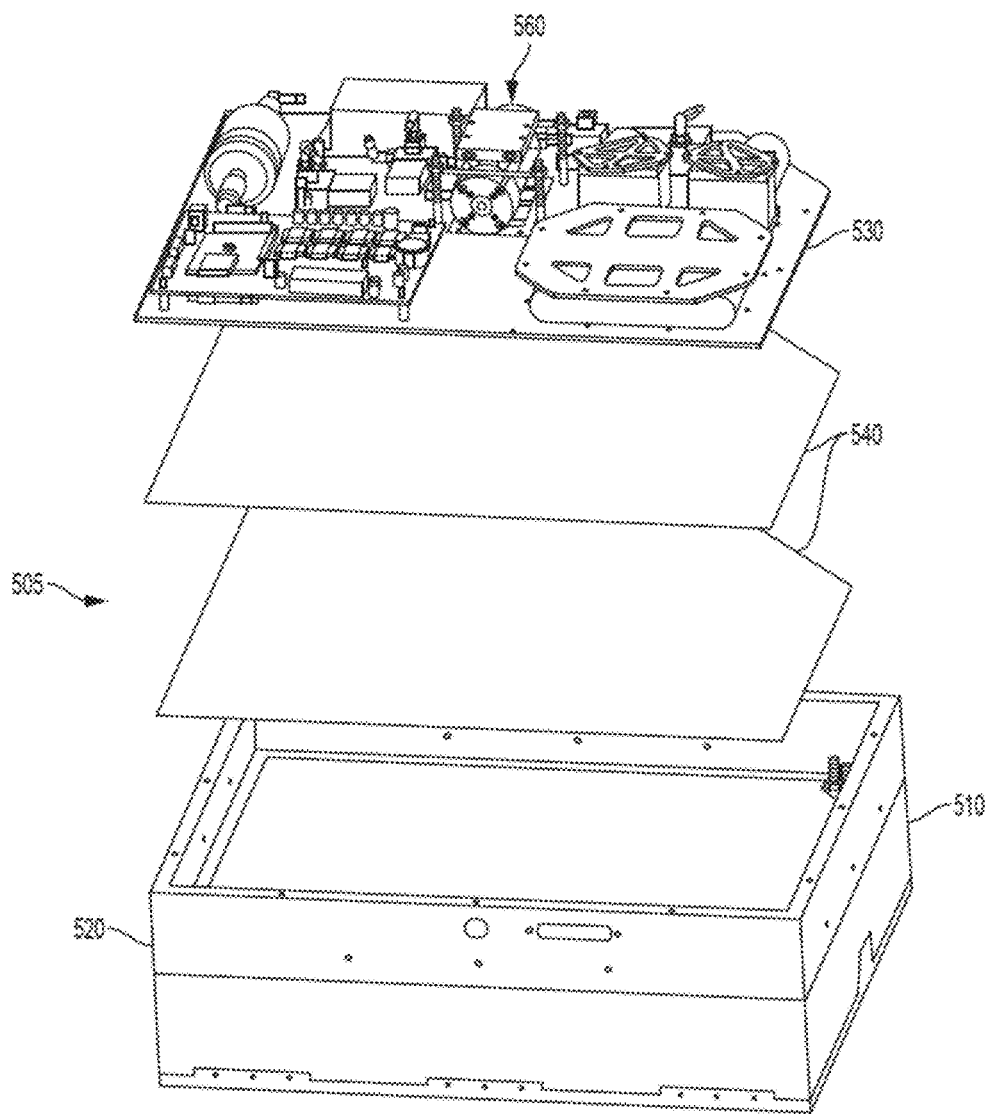
FIG. 5 is a representative illustration exploded view of a components chamber assembly for a sterilization device according to an example aspect.

FIG. 5 is an exploded view of components chamber assembly 520 of assembly of chambers 505. Assembly of chambers 505 includes sterilization chamber 510 and components chamber assembly 520. Components chamber assembly 520 includes mounting sheet assembly 530 and electrical insulating sheets 540. In an example aspect, components chamber assembly 520 serves as a base for sterilization chamber 510. Typically components chamber assembly 520 sits in the bottom of device housing (the housing, for example, case 350 as shown in FIG. 2A). FIG. 5, in other words, shows the assembly of chambers from the perspective of the bottom of the device. FIG. 5 includes a perspective view of mounting sheet assembly 530 including ozone generator 560. One or more channels, manifolds, hose barbs, and the like (not shown) may be provided for communication with sterilization chamber 510, and allow for passage of gases between components chamber assembly 520 and sterilization chamber 510.

Figure 6:
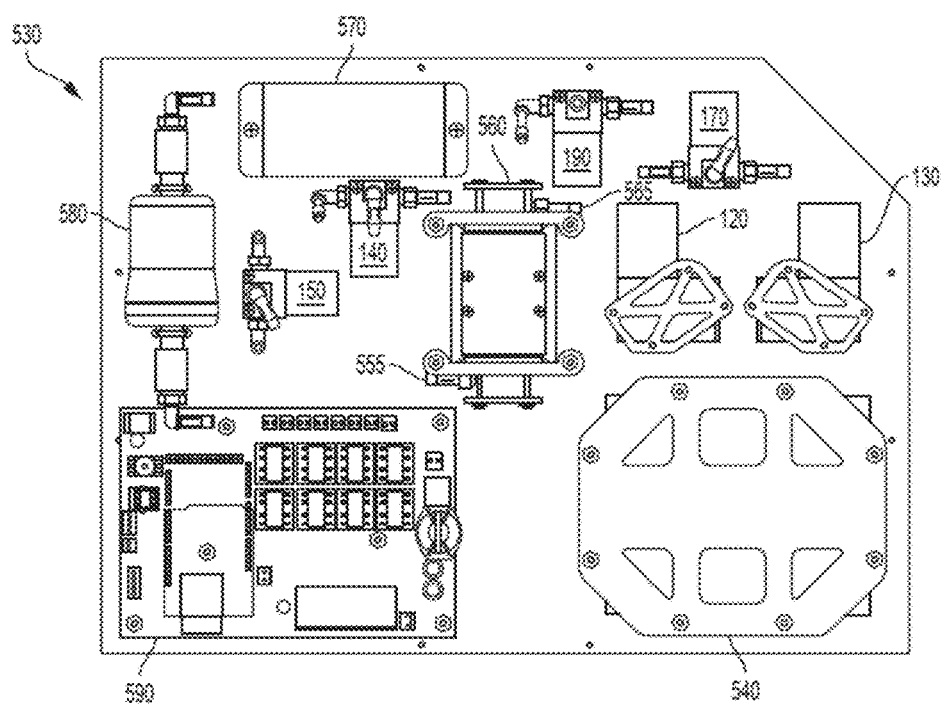
FIG. 6 is a representative illustration of a mounting sheet assembly for a sterilization device according to an example aspect.

Mounting sheet assembly 530, shown as illustrated in top view in FIG. 6, includes ozone generator 560, ozone generator transformer 570, and ozone scrubber 580. Mounting sheet assembly 530 further includes printed circuit board (PCB) 590 and battery 540. Mounting sheet assembly 530 also includes pump assemblies 120 and 130 as well as valves 140, 150, 190, and 170, shown also in FIGS. 1A and 1B.

The sterilization device does not require an external power source. In one embodiment the device includes a battery. As illustrated in FIG. 6, a sterilization device according to an example aspect is operated using battery power. In an example aspect, battery 540 is fixed to mounting sheet assembly 530. In an example aspect, the sterilization device includes an onboard secondary battery that may contain lithium iron phosphate and have a nominal voltage of about 12.8 VDC and about 9.9 A-Hr of charge capacity. In an example aspect, the battery is rechargeable with the capability to removably connect to an external power source. The battery may have a voltage of less than 18 volts. In one embodiment, the voltage is between about 10 and 15 volts. In one embodiment, the device of the present invention uses a Lithium iron phosphate secondary battery with a nominal voltage of 12.8V and 9.9 A-Hr capacity. The device may include a regulator to regulate the voltage to 12 VDC with a maximum current load of 5 A (60 W). The external power adaptor is configured for domestic and international use and accepts 85-264 VAC, 47-63 Hz providing 14.5 VDC at a max current of 10 A. The device can be charged while in operation at a maximum current of 4 A (58 W). At this rate the battery can be fully recharged in less than 2.5 hours even while running. In one embodiment, the maximum power consumption for running the device while charging is about 118 W.

In an example aspect, the sterilization device also includes adaptors to interface with the battery or power source. In an example aspect, the power source has a VDC (volts of direct current) of between about 9 and about 36 and may have at least about a 6 A discharge current capacity. In an example aspect, the sterilization device is configured with an AC wall adaptor. The wall adaptor is configurable to work with international power sources. Accordingly, the sterilization device is configured to receive power inputs of between about 85 to about 264 VAC, and between about 47 and about 63 Hz.

Figure 7:
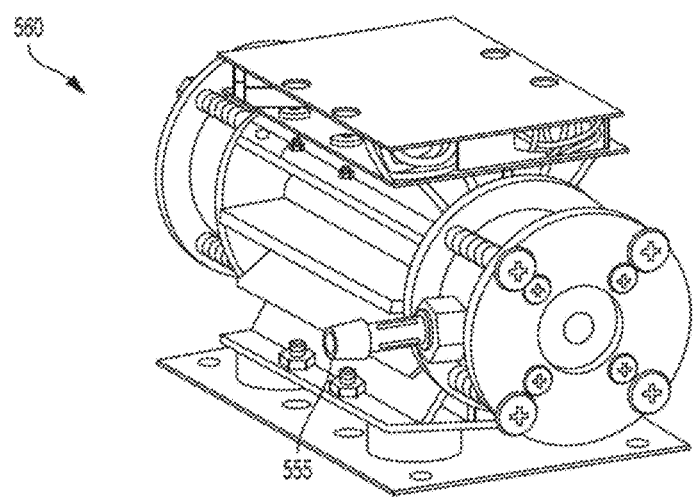
FIG. 7 is a representative illustration of an ozone generator for a sterilization device according to an example aspect.

The sterilization device does not require an external oxygen or air source, and may instead utilize oxygen present in ambient air present in the sterilization chamber (110, 210, 510) when the sterilization chamber (110, 210, 510) is sealed. In an example aspect, the portable sterilization device includes an ozone delivery device, wherein the ozone delivery device comprises a corona discharge ozone generator, a UV light ozone generator, a cold plasma ozone generator, a dielectric-barrier discharge ozone generator, an electrochemical ozone generator, or the like. Ozone delivery device is referred to as ozone generator interchangeably herein. Ozone generator 560, as shown also in FIGS. 5 and 6, is illustrated in FIG. 7. If desired, an oxygen generator or concentrator may be used to supply ozone generator 560 with supply air having a higher concentration of oxygen to improve the efficiency of ozone generator 560. Thus, for example, vacuum swing adsorption may be used to remove nitrogen from the air being used, thereby supplying a higher concentration of oxygen. Alternatively, a chemical reaction may provide a higher concentration of oxygen. As another example, an electrochemical oxygen generator may be used, such as a ceramic/solid state oxygen generator or a polymeric membrane oxygen generator. As still another example, oxygen may be generated using catalytic breakdown of the sterilant (e.g., hydrogen peroxide), such as using a platinum catalyst.

In an example aspect, the sterilization device utilizes a synergistic combination, within the sterilizing chamber, of ozone and hydrogen peroxide to produce a potent sterilant that is catalytically decomposed into to oxygen and water vapor at the end of the process. In an example aspect, ozone comes from a corona discharge. The ozone may be generated from ambient air fed through inlet 555 to ozone generator 560 and out through outlet 565 to inject via tubing to sterilization chamber (110, 210, 510) and or a valve similar to valve 170. Thus, in an example aspect, the valve includes an outlet for injecting air containing ozone to sterilization chamber 110 (or 210, 510). A separate valve may supply the ozone generator 560 and also includes an outlet for direct communication with a feed line to the sterilant delivery device or nebulizer, the nebulizer containing an aqueous hydrogen peroxide solution. Air not containing ozone is fed through the other valve for simultaneous nebulization with the hydrogen peroxide solution into a vapor. Alternately, air not containing ozone or only containing a small amount of ozone may be fed to the sterilant delivery device or nebulizer using one or more fans, blowers, or the like. Such air may be drawn from the sterilization chamber (110, 210, 510) and may optionally be passed through the breakdown catalyst 40 to eliminate or reduce ozone in the air passed to the sterilant delivery device or nebulizer. Ozone and hydrogen peroxide vapors are generated and mixed (peroxone) within the sterilization chamber (110, 210, 510), and not before. The resulting gas plasma contains highly oxidative chemical species. In an example aspect, the reactants used to produce the sterilant include ozone, ambient air, hydrogen peroxide, and water. The reaction produces numerous oxidizing species, transition species, and free radicals as products. The reaction may not be complete however and thus ozone, hydrogen peroxide, air, and water are all also potential products. The concentration of molecular ozone in the sterilization chamber during the sterilization cycle is in the range of 200 to 1500 ppmv based on conditions (relative humidity, pressure, temperature). This is the excess ozone as a product. In an example aspect, between about 200 and about 1500 ppmv of ozone is present. In an example aspect, the portable sterilization device includes an airflow circulation assembly comprising one or more pumps configured to circulate air through the sterilization device. Airflow circulation assembly is referred to as circulation element or circulator interchangeably herein. In an example aspect, the sterilization device includes a circulation element or circulator configured to continuously or intermittently circulate air through the device. The circulation element or circulator includes, for example, pumps, valves, fans, blowers, and tubing to circulate the flow of air, ozone, or both through the sterilization device.

In an example aspect, the sterilization chamber for sterilizing a plurality of medical instruments further comprises an ozone delivery device and a sterilant delivery device having a nebulization element or aerosolizing component, wherein the ozone delivery device and the sterilant delivery device are configured to deliver the aerosolized sterilant and ozone simultaneously into the instrument receptacle, where they only then mix to form the oxidative aerosolized sterilant. In an example aspect, the sterilization chamber for sterilizing a plurality of medical instruments further comprises an airflow circulation assembly comprising one or more pumps configured to circulate air through the sterilization chamber.

Figure 2B:
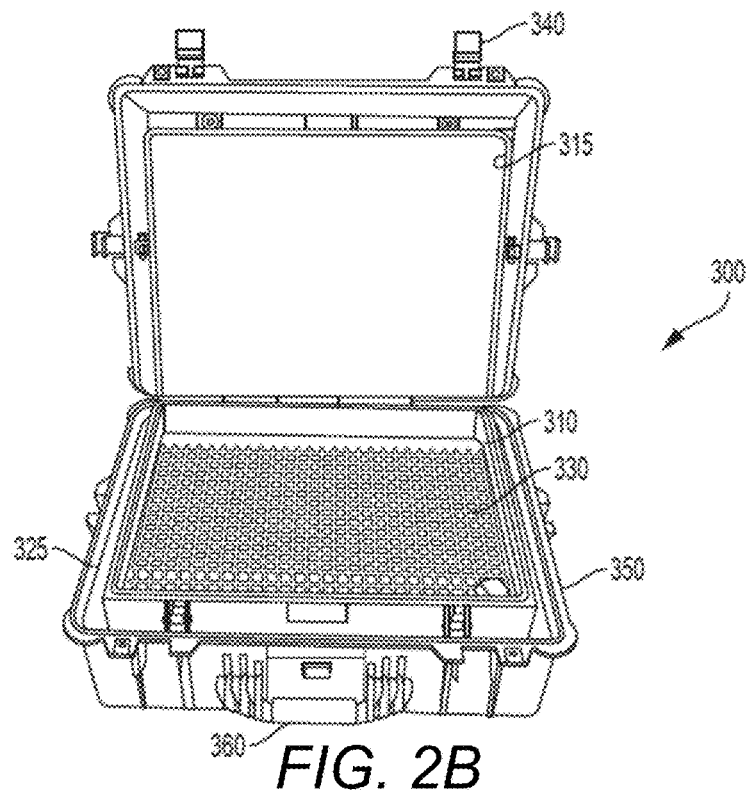
FIG. 2B is a representative illustration of a sterilization device according to an example aspect.
Figure 2C:
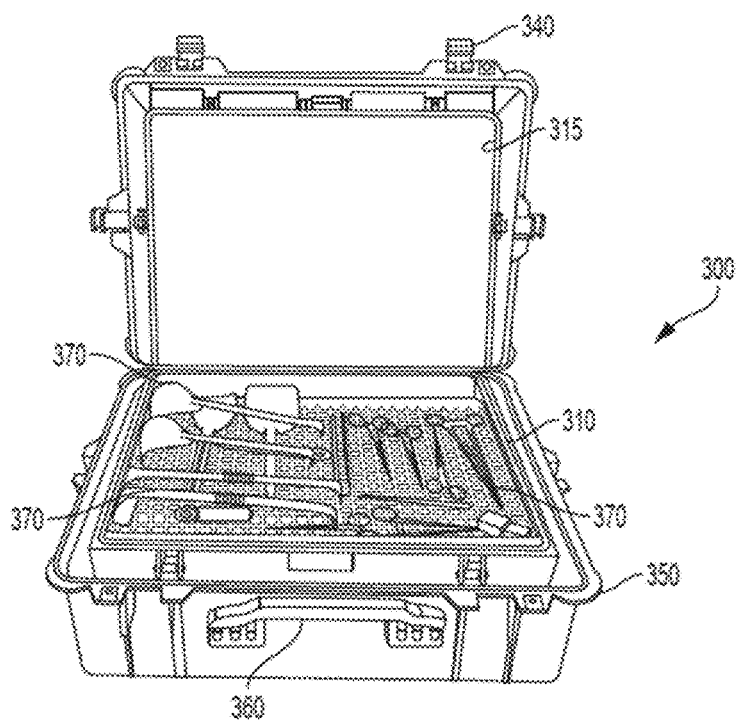
FIG. 2C is a representative illustration of a sterilization device containing surgical instruments according to an example aspect.

In an example aspect, the portable sterilization device includes a sealable sterilization chamber located within the external housing unit. As illustrated in FIG. 5, assembly of chambers 505 includes sterilization chamber 510 and components chamber assembly 520 for a sterilization device according to an example aspect. In an example aspect, the sterilization chamber is sealable. Sterilization chamber 510 includes a seal or an o-ring for sealing the sterilization chamber base to a sterilization chamber top (top 315 shown in FIGS. 2B and 2C). The sterilization chamber base and sterilization chamber top may have any complementary shape or size, including curved shapes, but the shape of sterilization chamber (110, 210, 510) illustrated in FIGS. 2A-2C is generally of a rectangular prism.

In an example aspect, at least a portion of the sterilant delivery device (180, 280) comprises a nebulization element that is contained within the sterilization chamber. Sterilization chamber 510 includes a sterilant outlet and potentially a portion of nebulization element or aerosolizing component. The nebulization element or aerosolizing component is also referred to as a nebulizer, mixer, or mixing element interchangeably herein. In an example aspect, the one or more sterilants comprise hydrogen peroxide contained within the nebulization element or aerosolizing component. In an example aspect, sterilant delivery device (180, 280) is a nebulizer. In an example aspect, sterilant delivery device (180, 280) is an ultrasonic nebulizer, a piezoelectric nebulizer, a mechanical nebulizer, a compressive nebulizer, a misting nozzle supplied by a pump, a misting nozzle supplied by a linear actuator, an ultrasonic spray nozzle, a Venturi nozzle, a microfluidic pin orifice, an air atomizing nozzle, a heat vaporizer, or a diesel fuel injector. The sterilant delivery device may be associated with a manifold having a plurality of ports or sterilant outlets, as discussed in more detail below. In an example aspect discussed in the prior application, the manifold has four ports: two straight and two right angle (90 degree ports), as. All four ports enter the manifold from the components chamber below via barbed fittings. One straight port enters the nebulizer or aerosolizing component from valve 170 when it is active. One straight port is open to the chamber and is connected to an air duct within tubing that is in communication with a pressure sensor (chamber pressure). One 90 degree port is open to the chamber providing a path for circulated air that bypasses the nebulizer; this is connected to valve 170 and is open when the valve is not active. One 90 degree port is open to the chamber providing a return path for circulated air. This port is connected to the air pumps which pull air from the chamber to circulate through the system. The air containing ozone, exiting the ozone generator bypasses the nebulizer or other aerosolizing component and is delivered directly to the sterilizing chamber through the manifold, meanwhile, air not containing ozone is delivered to the nebulizer or aerosolizing component. The plasma gas sterilant (i.e. ozone) and liquid sterilant (i.e. hydrogen peroxide) are only mixed within the sterilizing chamber 510, to maximize the effectiveness of the oxidative aerosolized sterilant so formed. Reactions are occurring throughout the sterilization chamber.

A sterilant delivery device includes a reservoir for holding a liquid sterilant, such as $H_2O_2$. The reservoir is configured for receiving $H_2O_2$ or other liquid sterilant. In an example aspect, the hydrogen peroxide is pre-loaded and contained within the storage element, or nebulizer. The sterilant delivery device further includes a removable top having a fill port or opening for receiving liquid sterilant. Air not containing ozone is received by the nebulizer through a feed line (not shown). The feed line connects, for example through valves (e.g., valve 170 of FIG. 1B) and tubing, the components chamber to the sterilization chamber when the sterilant delivery device 280 is located in the sterilization chamber. Air containing ozone exits the ozone generator in the components chamber assembly 520, may pass through a valve and then enters the sterilization chamber (110, 210, 510), potentially through a manifold that distributes the ozone to a plurality of locations in the sterilization chamber (110, 210, 510).

An air return from the chamber is attached directly to airflow circulation assembly (i.e. pumps 120, 130), which pulls air from sterilization chamber (110, 210, 510) and circulates it through the system. The airflow circulation assembly provides air flow paths through components that are in communication with the sterilization chamber. Manifolds may provide channels for the air flow paths into the and out of sterilization chamber (110, 210, 510). Also provided in manifold is a point where the chamber pressure is measured by a first pressure sensor.

Valves, hosing, and fittings as known in the art are useful in transporting the gas plasma sterilant (i.e. air containing ozone) to the sterilization chamber (110, 210, 510) and in transporting air not containing ozone to the nebulizer or other sterilant delivery device (180, 280) containing liquid sterilant (i.e. hydrogen peroxide). In one example, the air not containing ozone is circulated into the nebulizer and in combination with the liquid sterilant is compressively passed through the nebulizer, thus aerosolizing the mixture, for delivery into the sterilization chamber. In an example aspect, the compressive means of the nebulizer includes that air not containing ozone, leaving valve 170, is forced through a very narrow orifice thereby increasing pressure. The pressure oscillates a collar around the small orifice, which is in communication with the hydrogen peroxide solution. Connected to the air flow path between valve 170 and the narrow constriction within the nebulizer is a second pressure sensor that measures the backpressure produced by the compressive nebulizer. This measurement is useful for process control. The sterilant delivery device optionally includes baffles around nebulizer body to provide additional turbulence to the air flow leaving the nebulizer. This provides better distribution and mixing of the sterilant compounds.

In an example aspect, hydrogen peroxide is not present in excess once reacted with the gas plasma sterilant (ozone) and thus is optionally left over as a product of the reaction. In an example aspect, the device uses a pre-loaded measure of 4 mL of 7% aqueous hydrogen peroxide (93% water). Note that this measure of hydrogen peroxide is merely an exemplary feature of a single example aspect, and other example aspects may require or be capable of containing and/or using more or less or lesser or greater concentrations of hydrogen peroxide than 4 mL of 7% hydrogen peroxide. In an example aspect, the liquid sterilant solution is completely consumed during the mixing process. All of the products are involved in the sterilization mechanism of action to varying degrees. It will be appreciated by those of skill in the art that ozone and peroxide are also extremely potent for pollution abatement and will decompose any organic compounds in the ambient air.

In some embodiments, hydrogen peroxide constitutes all or part of a liquid sterilant useful in the sterilization device. Hydrogen peroxide, in the form of hydrogen peroxide dose packets, is pre-loaded in the sterilization device. In an example aspect, the hydrogen peroxide dose may be 4 mL of 7% aqueous hydrogen peroxide sealed in a packet or container. In an example aspect, the packet of hydrogen peroxide contains aqueous hydrogen peroxide ($H_2O_2$ and deionized water), including hydrogen peroxide ranging between 3% and 30% aqueous hydrogen peroxide. In another example aspect, the hydrogen peroxide is at most 8% aqueous hydrogen peroxide. In yet another example aspect, the hydrogen peroxide is about 7% aqueous hydrogen peroxide. The packets of hydrogen peroxide are filled and heat sealed. In an example aspect, the packet is configured such that the user can tear the packet open and add it to a nebulizer reservoir in the sterilization chamber prior to operation. For example, one entire packet is conveniently used for each sterilization cycle.

Figure 19:
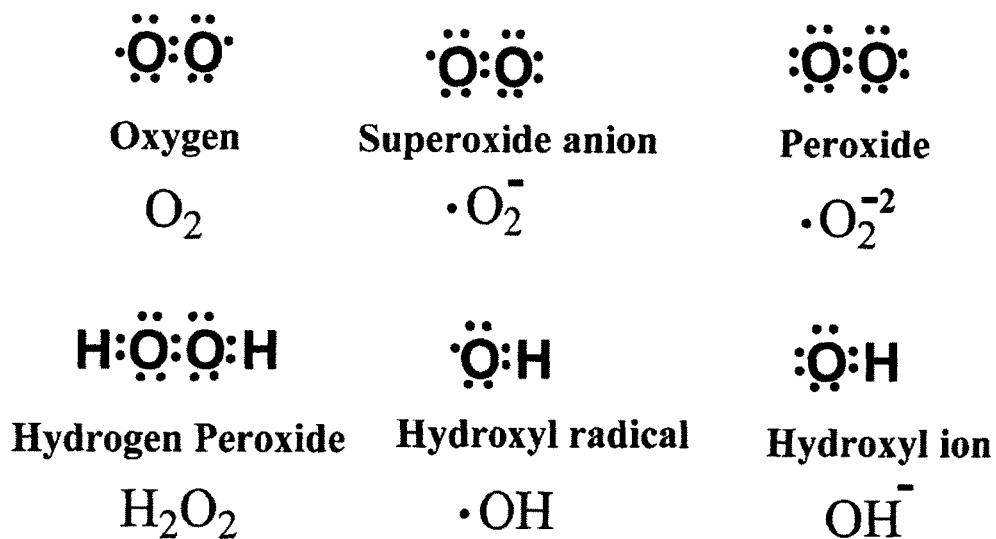
FIG. 19 is a representative illustration of reactive oxygen species (ROS) generated from molecular oxygen according to an example aspect.

Generally, the sterilants of the present disclosure generate reactive oxygen species (ROS) which can be used to kill various microbes, microorganisms, and pathogens. The phrase "reactive oxygen species" is used to describe a number of reactive molecules and free radicals derived from molecular oxygen. Their reactivity is generally due to their presence of an unpaired electron, which has potent degradation effects on a wide variety of substances. This degradation effect can often be measured in terms of a chemical's oxidation potential (e.g., the oxidative capacity of a given oxidizing agent). Molecular oxygen can be used to generate a number of ROS, including but not limited to, peroxide, hydrogen peroxide, nitric oxide, an oxygen ion, a hydroxyl ion, a hydroxyl radical, and superoxide, as shown in FIG. 19.

In some embodiments, the presence of a catalyst can augment the production of various ROS by shifting the dynamic equilibrium of a ROS reaction to the production of free radicals that can degrade various biomass materials. For example, in one embodiment of the present disclosure, hydrogen peroxide can be used to generate hydroxyl radicals in the presence of a transition metal catalyst. Without being limited to a particular catalyst, embodiments of the present disclosure can include catalysts that are comprised of one or more transition metals, such as but not limited to, Scandium, Titanium, Vanadium, Chromium, Manganese, Iron, Cobalt, Nickel, Copper, Zinc, Yttrium, Zirconium, Niobium, Molybdenum, Technetium, Ruthenium, Rhodium, Palladium, Silver, Cadmium, Hafnium, Tantalum, Tungsten, Rhenium, Osmium, Iridium, Platinum, Gold, and Mercury. Additionally, as would be readily recognized by one of ordinary skill in the art based on the present disclosure, catalysts of the present disclosure can be any heterogeneous mixture and/or combination of the above transitional metals, and may include other components that augment the catalytic process and the production of ROS. In some embodiments of the present disclosure, the catalyst is an iron-based catalyst and the iron-based catalyst interacts chemically with hydrogen peroxide in an aqueous solution to produce hydroxyl radicals that reduce the number of colony forming units (CFUs) for a given microbe or pathogen.

Figure 20:
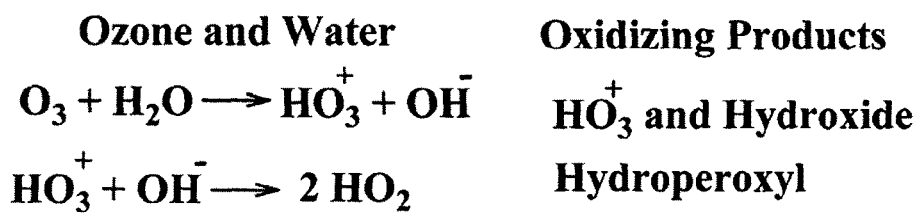
FIG. 20 is a representative illustration of various oxidizing products formed from the chemical reaction of ozone and water according to an example aspect.

In some embodiments, the nebulization element is configured to be operatively associated with a sterilization chamber and an ozone generator is also configured to be operatively associated with the sterilization chamber such that upon introduction of ozone from the ozone generator and an aerosolized sterilant from the nebulization element, ROS are produced in the sterilization chamber continuously. For example, in one embodiment, ozone and water can react throughout the sterilization chamber to kill various microbes, microorganisms, and pathogens. The chemical reaction of ozone and water can form various oxidizing products, including $HO_3^+$, hydroxide, and hydroperoxyl, as shown in FIG. 20.

Figure 21:
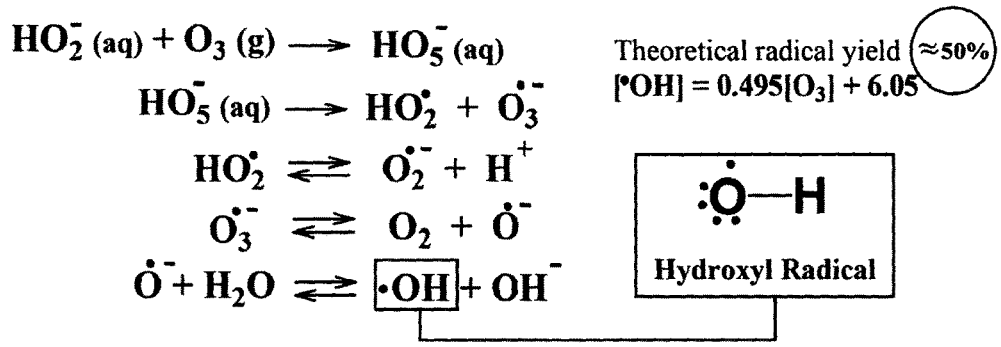
FIG. 21 is a representative illustration of various oxidizing products formed from the chemical reaction of ozone and hydrogen peroxide according to an example aspect.

In another embodiment, ozone and hydrogen peroxide (e.g., peroxone) can react within and throughout the sterilization chamber to kill various microbes, microorganisms, and pathogens. The chemical reaction of ozone and hydrogen peroxide can form various oxidizing products, including various hydroxyl radicals, as shown in FIG. 21.

The continuous production of the various oxidizing products from ozone and hydrogen peroxide by the devices and methods of the present disclosure can result in the synergistic elimination of pathogenic microorganisms. For example, the continuous production of oxidizing products from ozone and hydrogen peroxide by the devices and methods of the present disclosure can reduce both the overall quantities of pathogenic microorganisms and can reduce a greater variety of pathogenic microorganisms than exposure to either ozone or aerosolized hydrogen peroxide alone. In some cases, the continuous production of ROS from ozone and hydrogen peroxide by the devices and methods of the present disclosure can reduce the amount and varieties of pathogenic microorganisms in less time than exposure to either ozone or aerosolized hydrogen peroxide alone. In an example aspect, the number of pathogenic survivors is negatively correlated with increased hydrogen peroxide concentrations. In an example aspect in the range of 0 to 35% $H_2O_2$ by volume, the greater the concentration the more effective the sterilant. Furthermore, since the generation of the ROS from ozone and hydrogen peroxide first occurs within the sterilization chamber and not within the nebulizing element as in the prior application, the efficiency of the system is relatively increased, reducing the necessary time of exposure to achieve sterilization.

In one embodiment, the sterilization devices and methods of the present disclosure can inactivate a 6 log population of microorganisms determined to be most resistant organisms (MRO) to sterilization. For example, the sterilization devices and methods of the present disclosure can inactivate a 6 log population of (*Geobacillus Stearothermophilus*), identified as most resistant to the process, in 7.5 minutes of sterilant exposure time. In another example, stainless steel (316L) material coupons processed in the sterilization device of the present disclosure for 5 consecutive cycles received the best possible score of 0 when tested for cytotoxicity using the standard MEM elution protocol, wherein MEM stands for minimum essential medium. In yet another example, the simultaneous and continuous delivery of the oxidative aerosol sterilant and the ozone into the sterilization chamber containing a plurality of medical instruments at a pre-determined ozone concentration for a pre-determined time period is sufficient to obtain a sterility assurance level (SAL) of $10^{-6}$ for inactivation of a 6 log population of organisms determined to be most resistant organisms (MRO) to sterilization. In an example aspect, the sterilization device meets or exceeds biocompatibility criteria for passing of systemic toxicity, material mediated pyrogen, irritation, intracutaneous toxicity, cytotoxicity, and sensitization.

In an example aspect, the sterilization device includes a chemical indicator or other measurement element to determine or provide a measure of sterilant efficacy or other parameter. The chemical indicator or measurement element provides a parameter indicator of one or more separate elements of the sterilant. In an example aspect, a chemical indicator changes color under oxidation signifying a certain level of sterilant or sterilant component efficacy. Other indicators useful in the sterilization device include organic dyes that turn a lighter color, for example, when oxidized and/or in the presence of humidity. The user, or the device through a sensor, compares the color to a reference ring surrounding the indicator to determine if the process was effective. In an example aspect, chemical indicators are useful as a method or process validation and record retention (routine process monitoring) to demonstrate specified process conditions were met.

In an example aspect, the portable sterilization device further comprises a sterilant remediation element, wherein the sterilant remediation element and the airflow circulation assembly are operatively associated with the sealable sterilization chamber; and wherein the airflow circulation assembly is configured to cause air to flow from the sterilization chamber through the sterilant remediation element such that the air comprising the combination of the one or more sterilants and the ozone passes through the sterilant remediation element to facilitate breakdown of the one or more sterilants and the ozone into oxygen and water. In an example aspect, sterilant remediation element is referred to as breakdown catalyst interchangeably herein. In an example aspect, the sterilization device is configured to allow for an active breakdown of sterilant with catalyst after sterilization has taken place. This ensures minimizing the concentration of potentially harmful ozone vapors in the sterilization chamber and provides for safely opening the device for the removal of sterilized surgical instruments. In an example aspect, the sterilant remediation element comprises a metal-based catalyst that facilitates breakdown of the one or more sterilants and the ozone into oxygen and water. In an example aspect, the catalysts include one or more of manganese dioxide and copper oxide. In an example aspect, the sterilant is ozone. In another example aspect, the sterilant is a mixture of ozone and filtered ambient air circulating through the device.

In an example aspect, air is circulated through the sterilization device. In one embodiment, the sterilization device is configured to pull air from the sterilization chamber and direct it through tubing to components. This may be accomplished in a variety of ways, including using air pumps. Valves determine the flow path as controlled by a custom circuit board and software. In an example aspect, the valves include 3-way solenoid valves. The activation and inactivation of all components is controlled through a microprocessor that activates solid state relays to provide power to the component. In an example aspect, the power provided to each component is regulated to be consistently 12 VDC to maintain process consistency. During the sterilant generation and exposure phases, air is continuously circuited through an ozone generator and then directly to the sterilization chamber containing hydrogen peroxide from the ultrasonic nebulizer or other sterilant delivery device. The oxidative aerosolized sterilant is produced within the sterilization chamber as ozone reacts with hydrogen peroxide and water vapor and continues to be formed in cascading reactions within the sterilization chamber and on the surfaces of instruments. During the sterilant breakdown phase, air is diverted through the breakdown catalyst and continuously circulated until the ozone and peroxide concentrations are reduced to safe levels decomposing into oxygen and water vapor. In an example aspect, air leaving the catalyst is returned to the sterilization chamber though a separate port. Multiple pumps can be used during the breakdown phase to increase the decomposition rate as the air is circulated faster through the device. In an example aspect, entries (intake, nebulizer, exhaust, pressure duct) to the hermetically welded sterilization chamber are through one or more aluminum manifolds.

In an example aspect, there is a continuous mixing of hydrogen peroxide and ozone throughout the sterilization process. In an example aspect, dilute aqueous hydrogen peroxide is used; for example, the hydrogen peroxide may be less than 8% by volume. In other example aspects, hydrogen peroxide, ozone, and water are used to react together to form the sterilant. In an example aspect, the sterilant comprises a highly oxidative species. In an example aspect, the sterilant mixture is dispersed in the sterilization chamber with an ultrasonic nebulizer before any mixing with ozone occurs.

The sterilization process is performed using ambient air. In an example aspect, the air being used is the air residing inside the housing or case of the device. Thus, the sterilization device does not require supplemental air. In an example aspect, the device uses air with less than about 30% oxygen content. In an example aspect, the air is filtered inside the device as it circulates using an air filter or a particulate filter (30, 50 as shown in FIGS. 1A and 1B). The device of the present invention is configured such that no external oxygen source is required, no external water source is required, and no potable water is required. Accordingly, the case or housing of the device can be manufactured without inputs or connection fittings for these sources making manufacture easier and cheaper and facilitating the portability of the device and superior ingress protection.

Upon initiation of a sterilization method, when the sterilization chamber is sealed, the sterilization chamber will contain the object(s) to be sterilized as well as some ambient air. As the process starts, some of that ambient air may be evacuated, leaving the object(s) to be sterilized and remaining ambient air at some level of vacuum. As the aerosolized sterilant and ozone are dispensed or delivered to the sterilization chamber, the sterilization chamber will include the object(s) to be sterilized, gases including ozone, water (humidity) and gaseous byproducts of the reaction of sterilant and ozone, aerosolized sterilant and oxidative aerosol sterilant, aerosolized water, and liquid water that may have condensed on the sterilization chamber wall(s) and/or the objects to be sterilized. Discussion herein relating to the removal or withdrawal of "air" or "fluid" from the sterilization chamber, including through an "air return," and "air return inlet," or an "air return opening" is intended to embrace the passage of any fluid that may at the applicable time be within the sterilization chamber, including the original ambient air (gaseous) and gases containing ozone and/or aerosolized liquid components. Where such fluid is to be reused to supply an ozone generator, the fluid may be treated appropriately to maximize the efficiency of the ozone generator, including by filtering and/or drying the fluid/air before supplying it to the ozone generator.

In an example aspect, the device is configured to actively decompose the sterilant after use into oxygen and water vapor using a true catalyst, or in other words, a catalyst that is not consumed by the reaction. Accordingly, the catalyst need not be replaced or regenerated. In an example aspect, air is retained in the device as it is circulated through the catalyst until the amount of sterilant in the device reaches OSHA acceptable concentrations. This is an advantage over other devices that vent the ozone through a catalyst to the external environment because, for example, in prior art devices, air only passes once through a catalyst, which may be inefficient and insufficient to completely decompose the sterilant. The present sterilization device renders an ozone concentration that is harmless before opening of the sterilization device and releasing into the environment.

In an example aspect, the catalyst used to decompose the sterilant includes one or more of manganese dioxide and copper oxide. In embodiment that catalyst may be sold under the trademark HOPCALITE® owned by Mine Safety Appliance Company Corporation. In other example aspects, the catalyst is sold under the trademark CARULITE® owned by Carus Corporation.

The device hardware and software is designed to meet FDA requirements for sterilization of medical devices. Primarily that it consistently achieves lethality conditions for inactivation of organisms determined to be most resistant (MRO) to the process. The process is specified to achieve a sterility assurance level (SAL) of $10^{-6}$ for inactivation of a 6 log population of the MRO, or the probability of 1 survivor out of every 1,000,000 sterilization cycles. The most resistant organism to chemical and thermal sterilization processes is identified by the CDC and FDA as *Geobacillus stearothermophilus*. Biological indicators containing greater than a 6 log population of the MRO have been tested to determine the time required for inactivation under the device process conditions. Samples were exposed to the process for specified durations then transferred to growth media to determine whether any viable organisms remain. The samples are then incubated at optimal conditions for 7 days. If there are any viable organisms the solution will become turbid. If after 7 days the solution remains clear it is determined that all of the colony forming units (CFU) were inactivated. This Boolean (Pass or Fail) result indicates that the process was sufficient to inactivate a 6 log population. Sterilant exposure durations of 7.5 minutes have resulted in no growth of the indicator organism after 7 days of incubation. For FDA compliance the exposure time is then at minimum doubled to attain <overkill>, resulting in a SAL of $10^{-6}$.

Process conditions are controlled and monitored by the device during operation. Current sensors are used to measure the ozone generator load. The device is continuously monitoring feedback from these sensors to determine whether the generator output is within specified bounds. The applied potential of all active electrical components (solenoid valves, pumps, and ozone generator) is controlled at a constant 12 VDC via an onboard voltage regulator. The device will take a wide input range as low as 9 VDC and up to 250 VAC with the external power adaptor. An internal secondary battery can be used to power the device without an external power source. The battery state of charge is calculated with a fuel gauge integrated circuit (IC). The state of charge calculation is recorded in the data file and used for operational feedback. The device will prevent operation if the battery level is insufficient for an entire cycle when the external adaptor is not connected. When the power adaptor is connected a charge controller IC will limit the charging current to 4 A and indicate to the user that the battery is charging. With the power adaptor the device will charge the internal battery and can be operated simultaneously. A pressure transducer is connected to the sterilization chamber to measure vacuum level of the sterilization chamber relative to ambient. This sensor is used for leak detection. During operation the software continuously checks the relative vacuum, if the value is outside of the predetermined thresholds the device automatically initiates the sterilant breakdown routine and indicates to the user that the sterilization chamber pressure went out of range. Any sensor feedback indicating that the process conditions are out of a predetermined range will initiate the sterilant breakdown routine to permit safe opening.

In some embodiments, there is a different pressure transducer connected to the air flow path leading to the nebulizer or other sterilant delivery device (180, 280). Feedback from this transducer serves two purposes. A backpressure develops in the space where the sensor is attached due to the nebulizer constriction. If the nebulizer is malfunctioning or not properly attached the backpressure in this branch will be minimal or non-existent. If the backpressure value is outside of predetermined bounds, the device will initiate the breakdown routine and indicate to the user that the nebulizer is not attached correctly. The backpressure reading will also confirm that one or more valves is functioning properly and that the air flow within the device is compliant with the design parameters. If the valve is malfunctioning such that the air flow path is incorrect or partially obstructed the backpressure value will be out of range. Similar control and feedback systems are in place for sterilization chamber relative humidity, and temperature.

The device is intended for use in a wide range of environments. The device has been tested under numerous environmental conditions and is believed to be validated as safe and effective (as a sterilizer) over a specified range of ambient temperature, ambient humidity, and barometric pressure. The device utilizes onboard sensors to measure all of these values in real time. This feedback is incorporated into the device operation and recorded in the header of data files for subsequent sterilization cycles. If any of the ambient temperature, ambient humidity, or barometric pressure readings are outside of the predetermined bounds the device will prevent initiation of a sterilization cycle and notify the user which of the condition are out of range.

Once the sterilant exposure and breakdown phases are complete the device will stop and indicate to the user that the load is sterile and ready for use. The device will maintain the relative vacuum within the sterilization chamber for a predetermined period or until the user acknowledges the feedback and presses a button to permit opening of the sterilization chamber and use of the sterilized instruments. This feature allows for the sterilization chamber to act as one large sterile barrier for a predetermined duration following sterilization in the event that the user is not ready to use the instruments that were sterilized. The sterile barrier will be tested using an aerosolized spore suspension with a method known as the package integrity test standard for sterile barriers and packaging.

Figure 8:
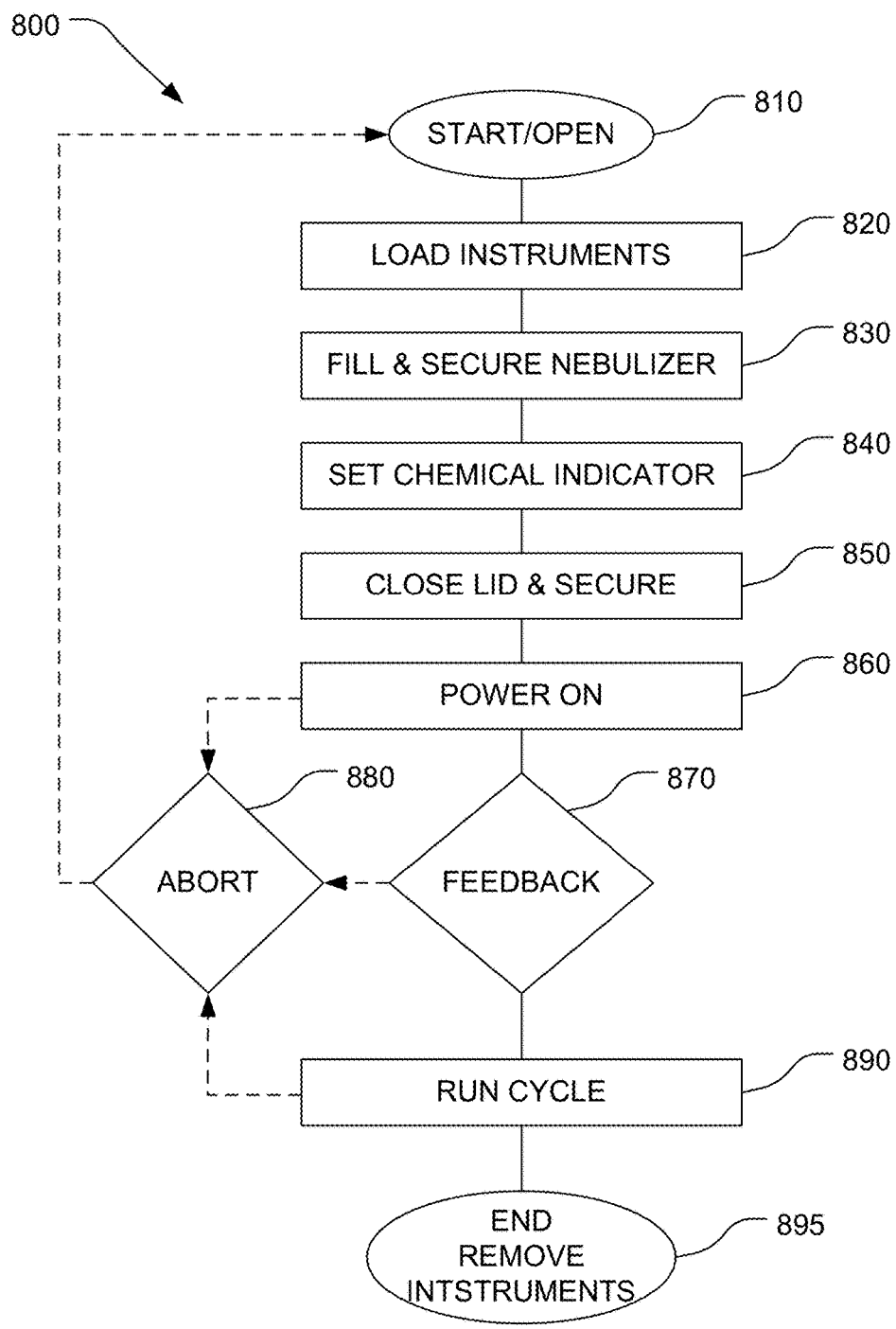
FIG. 8 is a flow chart illustrating use of the sterilization device according to an example aspect.

FIG. 8 is a flow chart illustrating use and operation of the sterilization device according to an example aspect. At any time, if needed, a user can abort a cycle at step 880 and run the breakdown phase. Safety features prevent the system from opening until breakdown phase is finished. A user prepares the sterilizer for use by setting the case on a level or substantially level surface, opening external latches on housing or case, and lifting the lid to expose the sterilization top. Then the user opens the four internal latches and lifts the sterilization chamber lid to inspect the chamber, which should be clean and dry, as in step 810. The user then loads the sterilization chamber with cleaned and dry stainless steel and/or tungsten carbide surgical instruments, for example, as in step 820. Instruments should be spaced so that the instruments are not touching and all jaws and clamps are open and not engaged. In step 830, user checks that the sterilant delivery device or nebulizer is completely empty and dry. If needed, sterile dressing is used to dry the reservoir. The user then adds the entire contents of one ROSS M 1 solution sachet (7% hydrogen peroxide) into the nebulizer reservoir. The user then ensures nebulizer top is placed securely on base and secured firmly to manifold. In step 840, the user optionally places a chemical indicator face up in front left corner of chamber. The user then closes the sterilization chamber lid and secures all four latches as in step 850. The user then presses the power switch on the control panel to power the device ON in step 860. To initialize the sterilization device, the user presses and holds the 'Wake' button for 3 seconds. To start a cycle, from the main menu, the user presses and holds the 'Start' button for 3 seconds. As in step 870, the feedback display then prompts the user to press 'Yes' to confirm ROSS MI solution was added. Feedback display also prompts the user to press 'Yes' to start cycle 'Automated Operation', as in step 890. Step 890 includes the breakdown cycle to return the sterilization chamber to a safe level of ozone. When complete, two tones sound and the feedback display reads 'Sterilization Complete', at which time the user presses 'Yes' to Open, and then instruments may be removed in step 895, with the instruments available at that time for immediate use. As mentioned, sterilization process may be aborted if needed as in step 880. To initiate the sterilant breakdown phase at any time, the user presses and holds the red 'Abort' button for 3 seconds, at which time the system will display: 'ERROR: Aborted, Ozone Above PEL, Do Not Open'. In an example aspect, the system will prevent normal operation if there is an initial vacuum within the chamber. The system will display: ERROR: Chamber Pressurized, at which time the user runs the breakdown phase to return sterilant concentrations to a safe level and equilibrate the chamber pressure. In the event of power failure, the user holds the 'Abort' button for 3 seconds to initiate the sterilant breakdown phase from the main menu. The load is not ready for use and must be reprocessed. In the event the battery dies during operation, the user switches OFF the power, attaches the power adaptor, plugs in the power supply, switches ON the power, wakes the device (hold wake for 3 seconds), and initiates the breakdown phase (hold Abort for 3 seconds). In the event power is not available, the user leaves the system closed and inactive until the device can be connected to power.

In an example aspect a method comprising manufacturing a portable sterilization device comprising is provided. In an example aspect, the method includes manufacturing a portable sterilization device comprising an external housing unit; a sealable sterilization chamber located within the external housing unit; a sterilant delivery device operatively associated with the sterilization chamber, the sterilant delivery device comprising a nebulization element and one or more sterilants, wherein the nebulization element is configured to convert the one or more sterilants into an aerosol sterilant and deliver the aerosol sterilant into the sterilization chamber; an ozone delivery device operatively associated with the sterilization chamber, the ozone delivery device configured to deliver ozone into the sterilization chamber; an airflow circulation assembly; a control panel configured to operate the sterilization chamber, the sterilant delivery device, the ozone delivery device, and the airflow circulation assembly, wherein the control panel is further configured to execute an operation to deliver the aerosol sterilant and the ozone simultaneously into the sterilization chamber, where an oxidative aerosol sterilant is thereby created; and a power source operatively associated with the control panel and configured to supply power to the sterilization chamber, the sterilant delivery device, the ozone delivery device, and the airflow circulation assembly.

In an example aspect, the method includes wherein at least a portion of the one or more sterilants comprise hydrogen peroxide. In an example aspect, the method includes wherein the sterilant delivery device comprising the nebulization element is contained within the sterilization chamber. In another example aspect, the method includes wherein the sterilant delivery device comprising the nebulization element is at least partially contained within the sterilization chamber. In yet another example aspect, the method includes wherein at least a portion of the sterilant delivery device (such as at least a portion of the nebulization element, such as a sterilant outlet or a portion thereof) is contained within the sterilization chamber. In an example aspect, the method includes wherein the one or more sterilants comprise hydrogen peroxide contained within the nebulization element. In an example aspect, the nebulization elements comprises a device such as an ultrasonic nebulizer, a piezoelectric nebulizer, a mechanical/compressive nebulizer, a fogging or misting nozzle with a linear actuator to create pressure for delivery, a fogging or misting nozzle with a pump or diaphragm, an ultrasonic spray nozzle, an air atomizing nozzle, a Venturi nozzle, a microfluidic pin orifice, a heat vaporizer, or a diesel fuel injector.

In an example aspect, the method includes wherein the ozone delivery device comprises a device such as a corona discharge ozone generator, a UV light ozone generator, a cold plasma ozone generator, or a dielectric barrier ozone generator. In another example aspect, the method includes electrochemical cogeneration of ozone and sterilant (hydrogen peroxide). In an example aspect, the method includes wherein the airflow circulation assembly comprises one or more pumps configured to circulate air through the sterilization device. In an example aspect, the method includes wherein the portable sterilization device further comprises a sterilant remediation element, wherein the sterilant remediation element and the airflow circulation assembly are operatively associated with the sealable sterilization chamber; and wherein the airflow circulation assembly is configured to cause air to flow from the sterilization chamber through the sterilant remediation element such that the air comprising the combination of the one or more sterilants and the ozone passes through the sterilant remediation element to facilitate breakdown of the one or more sterilants and the ozone into oxygen and water. In an example aspect, the method includes wherein the sterilant remediation element comprises a metal-based catalyst that facilitates breakdown of the one or more sterilants and the ozone into oxygen and water. In an example aspect, the method includes wherein the portable sterilization device further comprises one or more sensors operatively associated with the control panel and configured to monitor one or more operational parameters of the device. In an example aspect, the method includes wherein the one or more operational parameters comprise one or more of closure integrity, sterilant levels, ozone levels, airflow velocity, air pressure, valve operation, temperature, humidity, power levels, electrical current, device operation, sterilization cycle lengths, and sterilization cycle number.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting aspects or features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_1+k*(R_u-R_l)$, wherein k is a variable ranging from 1 percent to 100 percent with a 1 percent increment, i.e., k is 1 percent, 2 percent, 3 percent, 4 percent, 5 percent, ..., 50 percent, 51 percent, 52 percent, ..., 95 percent, 96 percent, 97 percent, 98 percent, 99 percent, or 100 percent.

Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present disclosure.

The present disclosure, in various aspects, embodiments, and configurations, includes components, methods, processes, systems and/or apparatus substantially as depicted and described herein, including various aspects, embodiments, configurations, sub combinations, and subsets thereof. Those of skill in the art will understand how to make and use the various aspects, aspects, embodiments, and configurations, after understanding the present disclosure. The present disclosure, in various aspects, embodiments, and configurations, includes providing compositions and processes in the absence of items not depicted and/or described herein or in various aspects, embodiments, and configurations hereof, including in the absence of such items as may have been used in previous compositions or processes, e.g., for improving performance, achieving ease and\or reducing cost of implementation.

As discussed above, one of the improvements implemented in example aspects of the present disclosure over the disclosure of the prior application is the delivery of the sterilant to the sterilization chamber before any mixing of the sterilant with ozone, such that formation of the short-lived oxidative aerosolized sterilant occurs within the sterilization chamber, thereby maximizing efficiency of the sterilization process.

Another improvement that may be implemented in example aspects of the present disclosure is using the placement, orientation, and number of sterilant outlets, ozone outlets, and air flow return inlets to control the distribution and movement of reagent components (ozone and sterilant) and the generated oxidative aerosolized sterilant throughout the sterilization chamber so as to control the production and refreshing of reactive oxygen species within the sterilization chamber. As the various reactive species, airflow, and humidity within the chamber is controlled, the overall lifetime and effectiveness of the generated oxidative species is maximized, as is the period of time in which the species is capable of being in contact with surfaces to be sterilized. Accordingly, all variables may be optimized, including variables of flow, temperature, humidity, sterilant concentration, ozone concentration, and mixing of sterilant and ozone within the sterilization chamber.

One of the ways in which the distribution of ozone and sterilant can be controlled is by varying the number, orientation, and/or location of sterilant outlets and ozone outlets within the sterilant chamber, as well as by varying the number and/or location of air return inlets within the sterilant chamber. When multiple ozone outlets are provided, they may be linked to the ozone generator using a manifold that distributes the ozone from the ozone generator to the various ozone outlets. Alternatively, multiple ozone generators may be utilized, with each ozone generator's output being fluidly connected to one or more ozone outlets in the sterilization chamber. When multiple sterilant outlets are provided, they may similarly be connected to a single sterilant delivery device through a manifold, separate individual sterilant delivery devices may be provided to each sterilant outlet, or multiple sterilant delivery devices may each supply a subset of the sterilant outlets.

Where multiple air return inlets are provided, they may be linked using a manifold to one or more pumps that return the air from the sterilization chamber to be reused in the process as discussed above.

FIGS. 9-18 illustrate possible configurations for an exemplary rectangular sterilization chamber 900, of ozone outlets 910, sterilant outlets 920, and air return inlets 930. As discussed above, the ozone outlets 910, sterilant outlets 920, and air return inlets 930 may be varied in their locations within the sterilization chamber 900, and any of the ozone outlets 910, sterilant outlets 920, and air return inlets 930 may be located on any wall of the sterilization chamber 900. Accordingly, any two-dimensional configurations illustrated in FIGS. 9-18 should be understood as being shown for representational purposes, only, and it should be understood that variations in three dimensions are also embraced by alternate aspects of the present disclosure.

Figure 9:
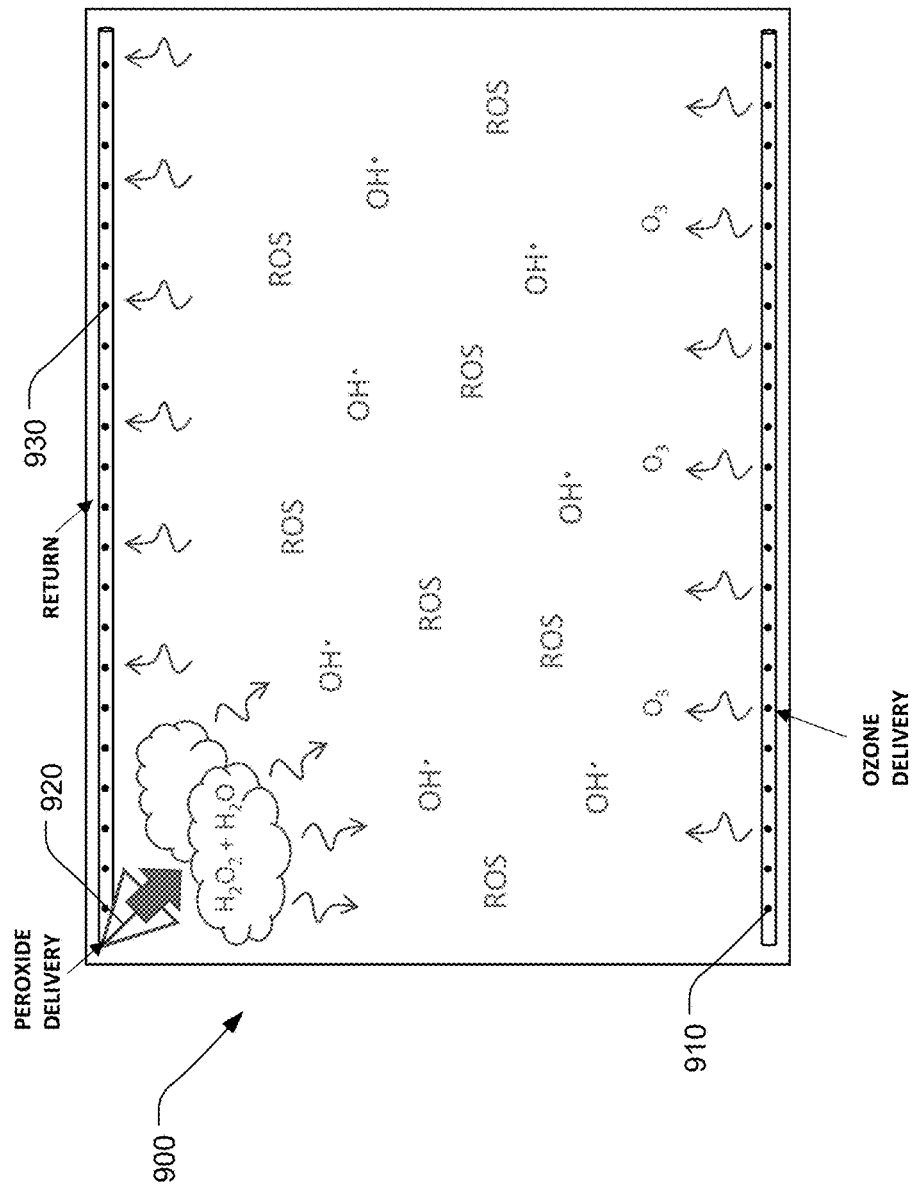
FIG. 9 is a representative illustration of a possible configuration of the disposition and arrangement of ozone outlets, a sterilant outlet, and air return inlets according to an example aspect.

FIG. 9 illustrates an example aspect of the present disclosure in which there is a single sterilant delivery outlet 920 generally disposed in one corner of the sterilization chamber 900. In this example aspect, there are multiple ozone outlets 910 disposed along one side of the sterilization chamber 900, fed by a linear manifold. There are also multiple air return inlets 930 disposed along another side of the sterilization chamber 900 opposite the ozone outlets 910. Accordingly, airflow within the sterilization chamber 900 is generally in one direction from the ozone outlets 910 to the airflow inlets 920 in this example aspect.

Figure 10:
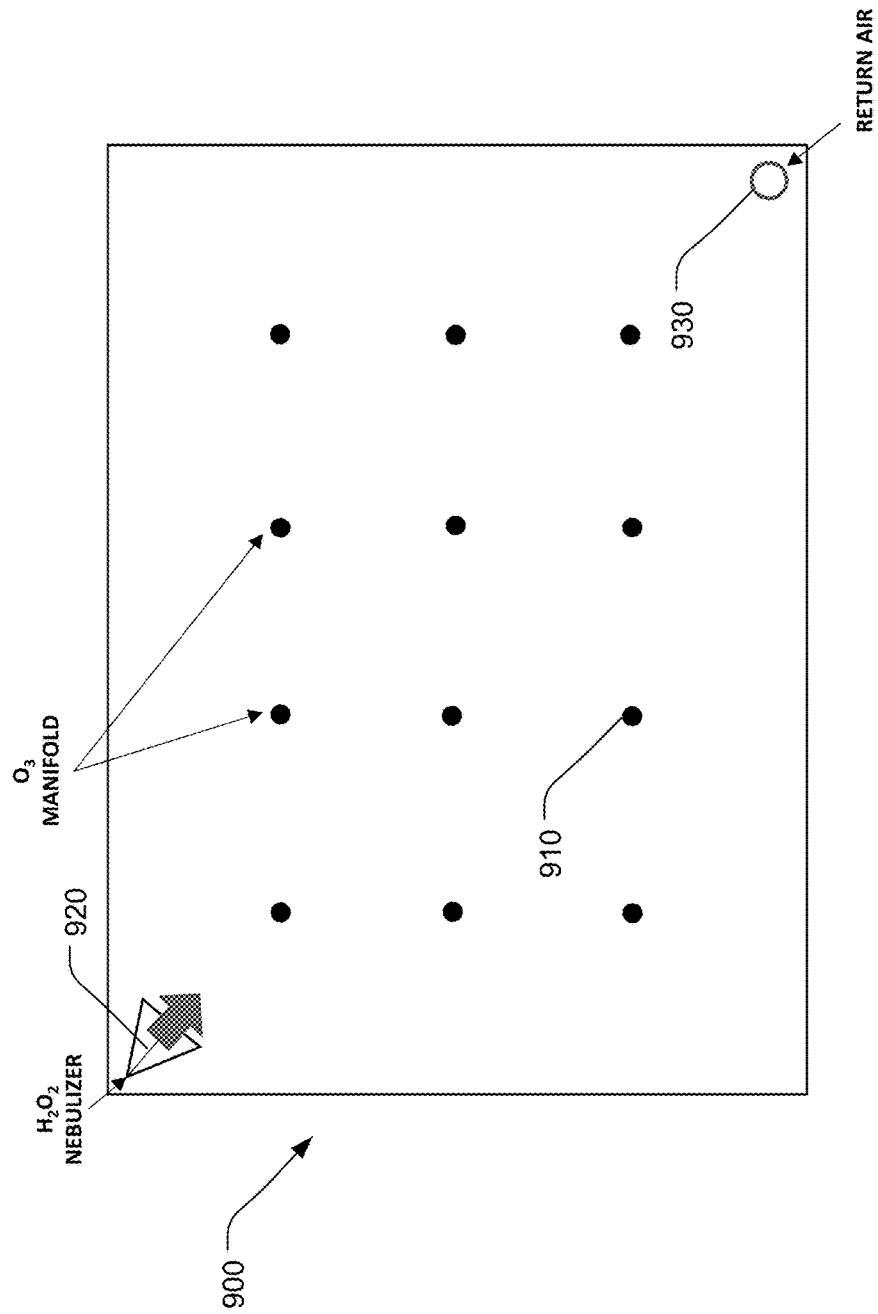
FIG. 10 is a representative illustration of an alternate possible configuration of the disposition and arrangement of ozone outlets, a sterilant outlet, and an air return inlet according to an example aspect.

FIG. 10 illustrates an alternate example aspect with a single sterilant delivery outlet 920 at one corner of the sterilization chamber 900 and a single airflow inlet 930 at an opposite corner of the sterilization chamber 900. In this example aspect, there are multiple ozone outlets 910 distributed generally evenly throughout the sterilization chamber 900 in a grid pattern. The exact number of ozone outlets 910 shown is intended only to be illustrative, and is not limiting of the number of ozone outlets 910 that could be used in other example aspects of the disclosure.

Figure 11:
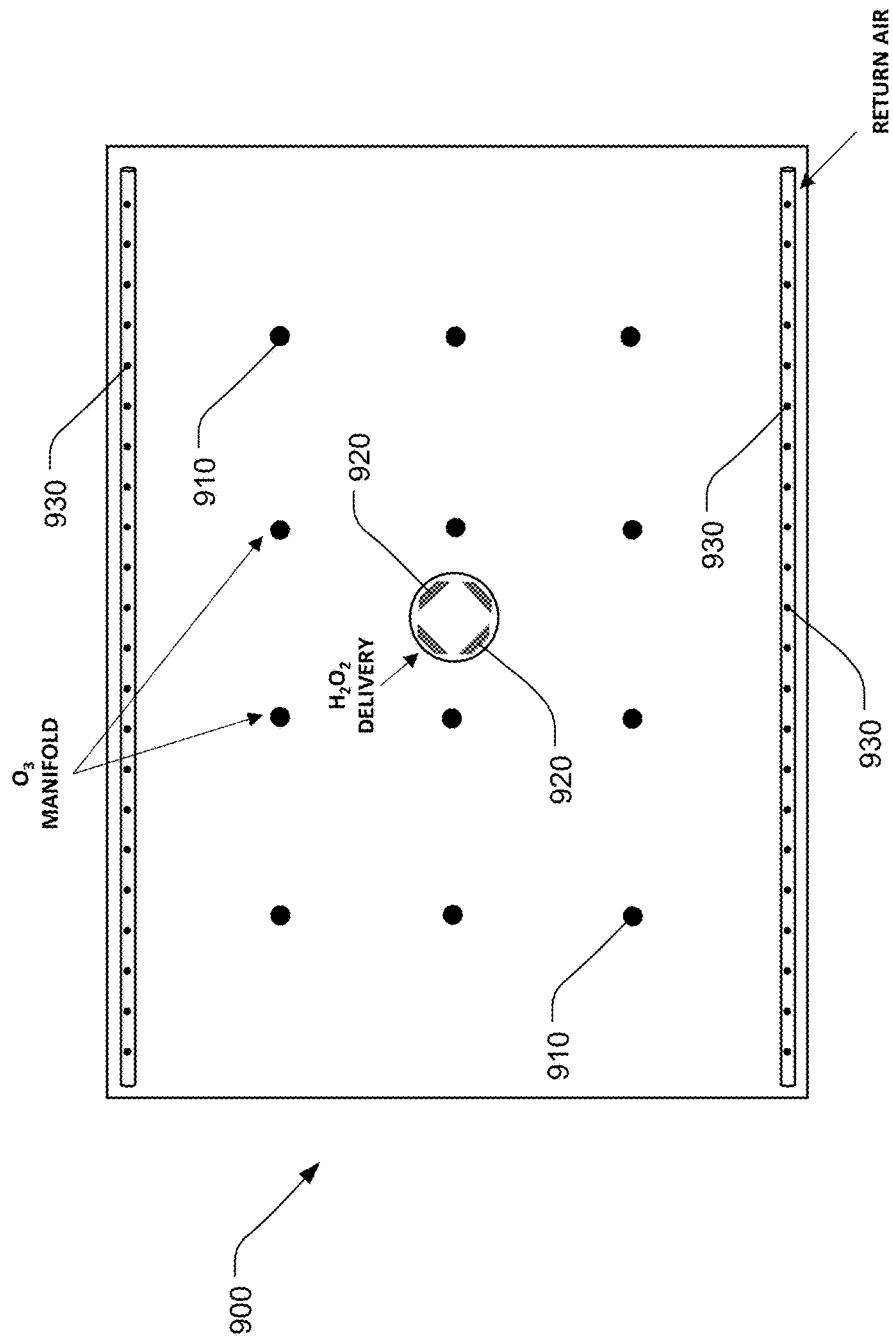
FIG. 11 is a representative illustration of an alternate possible configuration of the disposition and arrangement of ozone outlets, sterilant outlets, and air return inlets according to an example aspect.

FIG. 11 illustrates an alternate example aspect in which a single, centrally-located sterilant delivery device has four sterilant outlets 920 oriented to maximize dispersal of sterilant throughout the sterilization chamber 900. The example aspect also includes a grid of generally evenly spread ozone outlets 910. In the example aspect, multiple air return inlets 930 are provided along two of the sides of the sterilization chamber 900.

Figure 12:
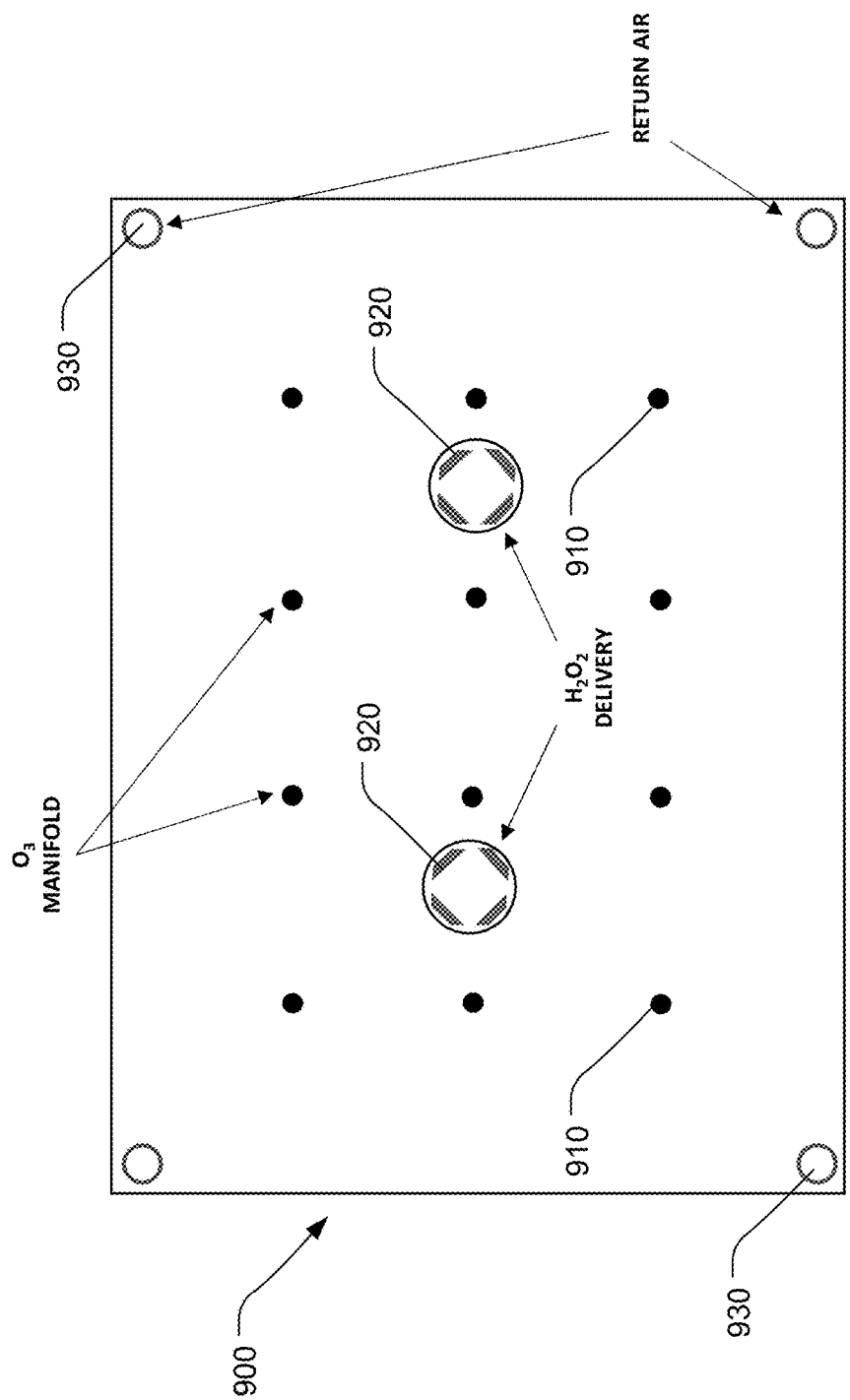
FIG. 12 is a representative illustration of an alternate possible configuration of the disposition and arrangement of ozone outlets, sterilant outlets, and air return inlets according to an example aspect.

FIG. 12 illustrates an alternate example aspect in which two sterilant delivery devices each have four sterilant outlets 920 oriented to maximize dispersal of sterilant throughout the sterilization chamber 900. The ozone outlets 910 are again dispersed on a grid connected by an ozone manifold (not shown). In this example aspect, four air return inlets 930 are located near the four corners of the sterilization chamber 900.

Figure 13:
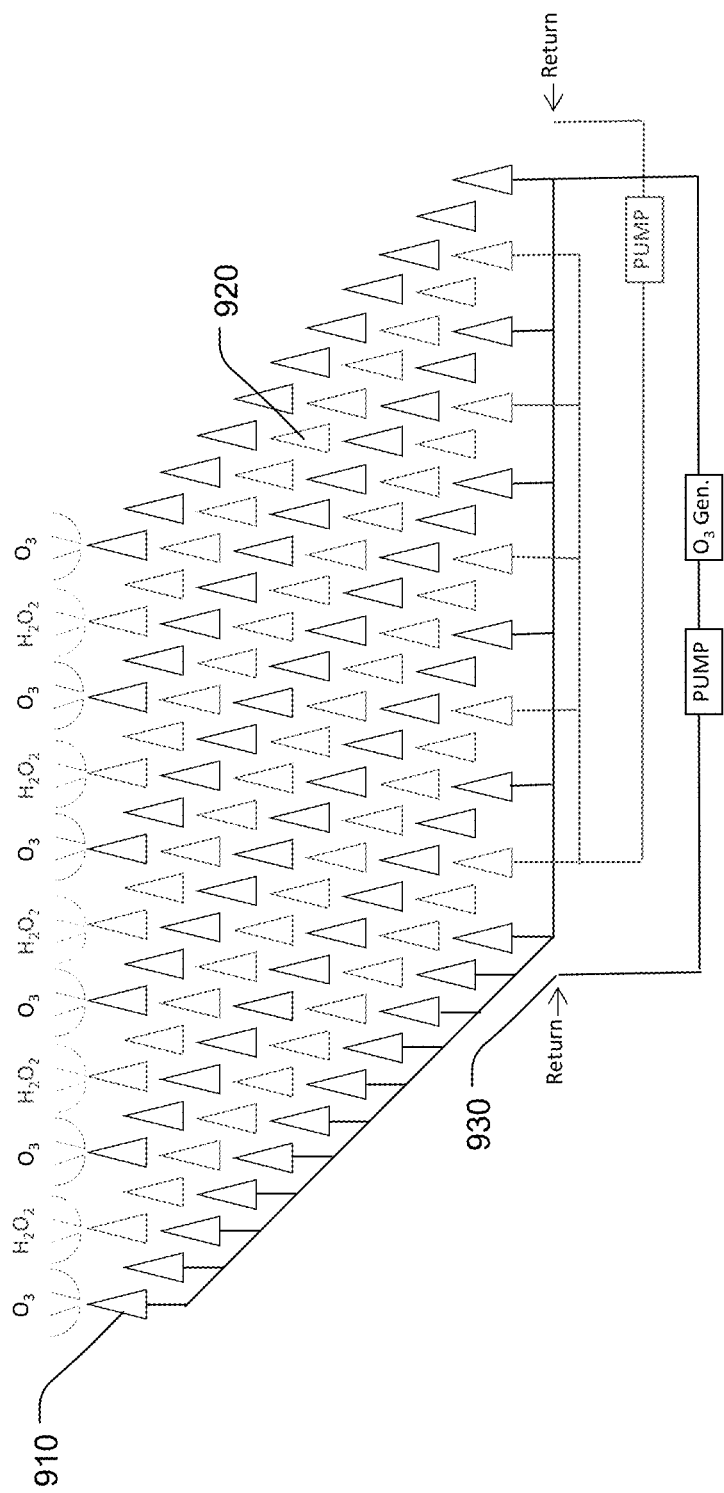
FIG. 13 is a representative illustration of an alternate possible configuration of the disposition and arrangement of ozone outlets, a sterilant outlet, and air return inlets according to an example aspect.
Figure 14:
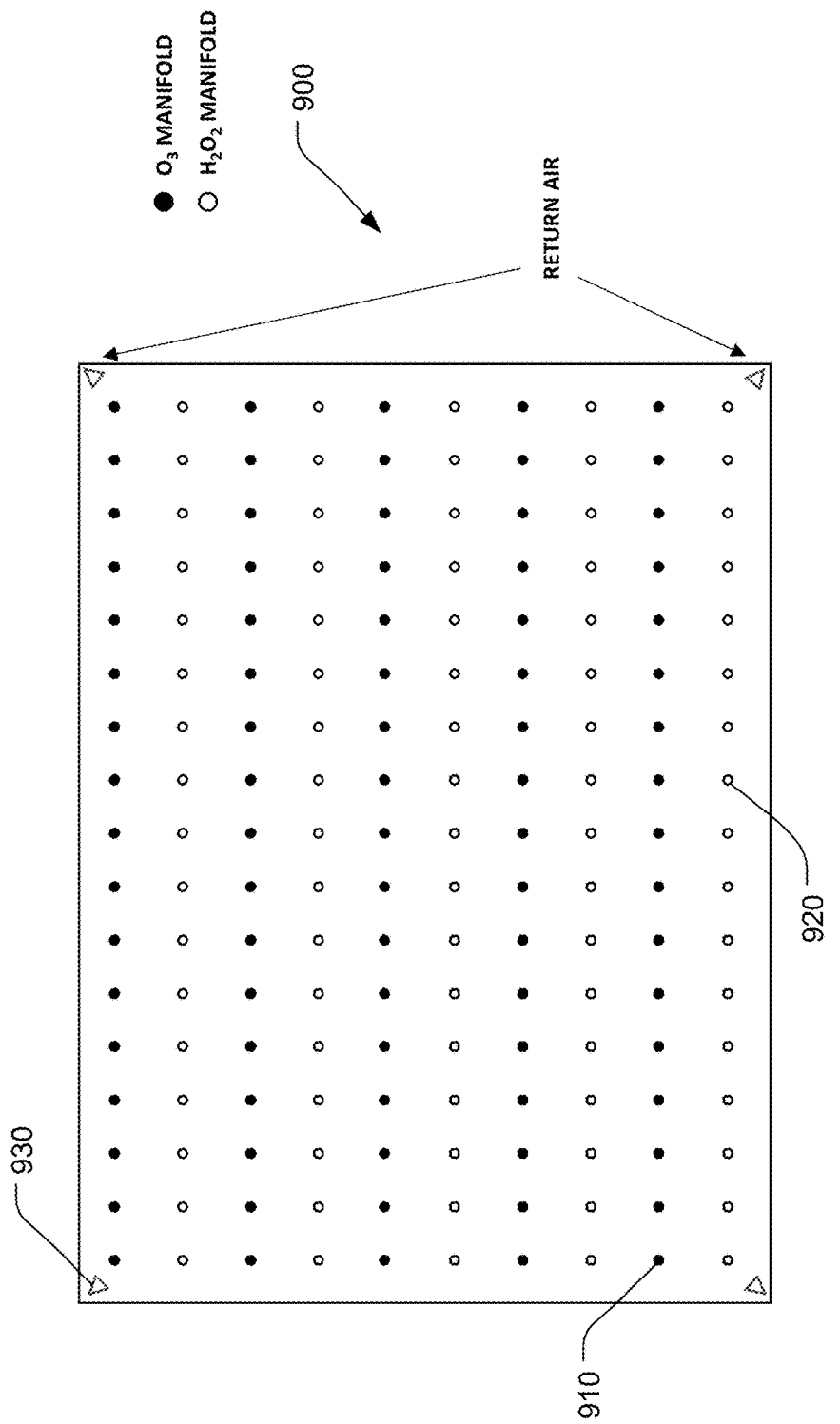
FIG. 14 is a representative illustration of an alternate possible configuration of the disposition and arrangement of ozone outlets and sterilant outlets according to an example aspect.
Figure 15:
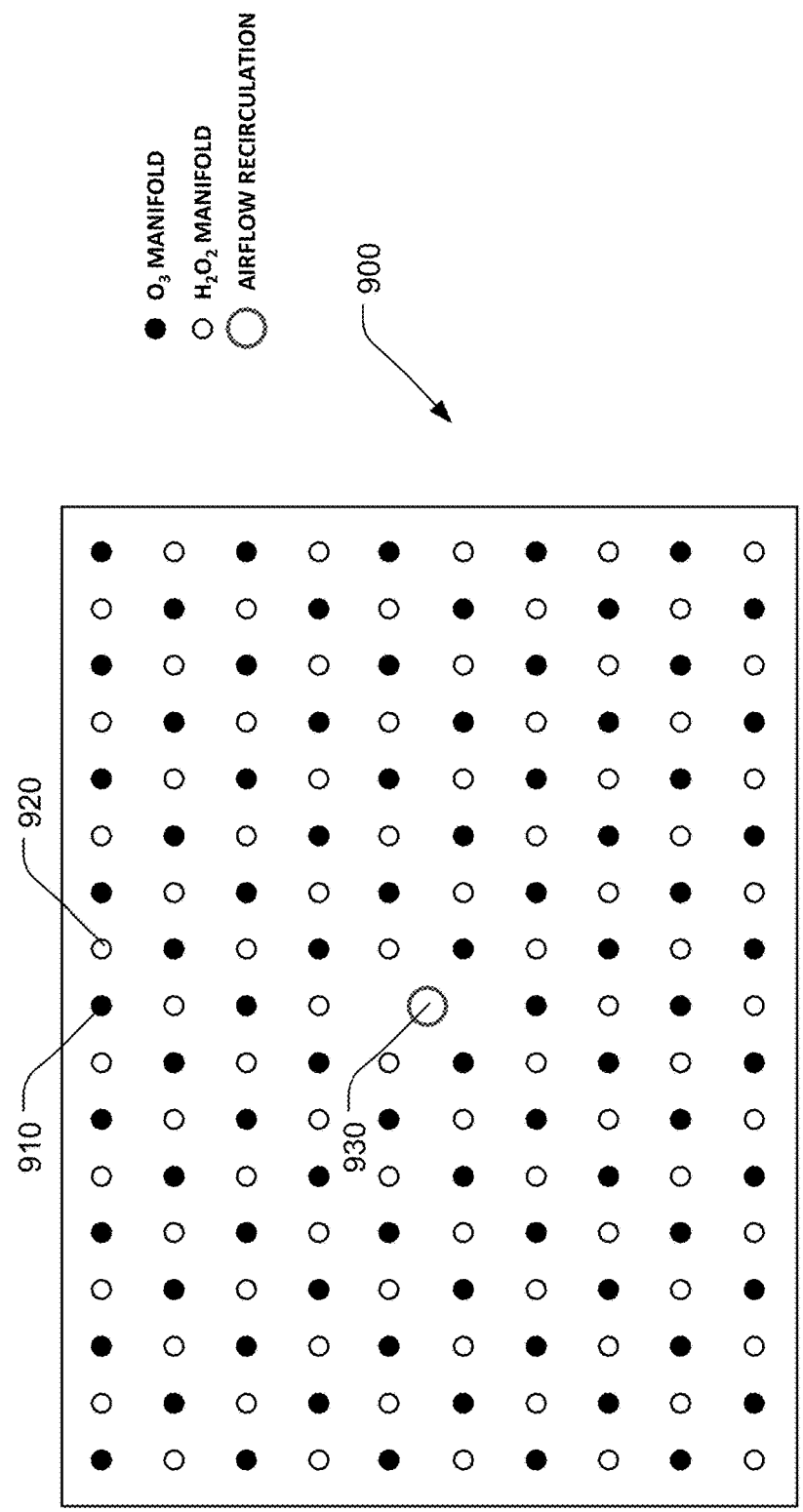
FIG. 15 is a representative illustration of an alternate possible configuration of the disposition and arrangement of ozone outlets, sterilant outlets, and air return inlets according to an example aspect.
Figure 16:
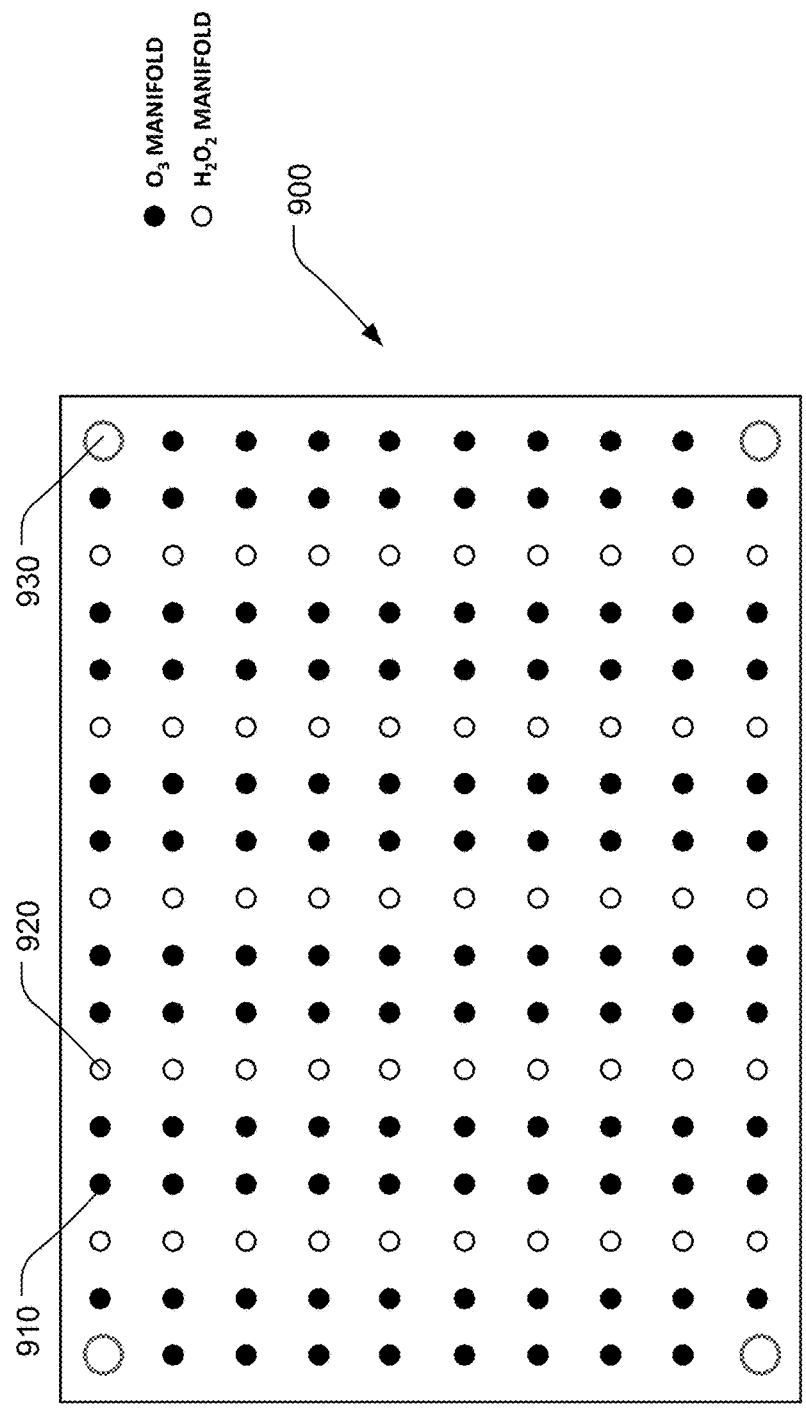
FIG. 16 is a representative illustration of an alternate possible configuration of the disposition and arrangement of ozone outlets, sterilant outlets, and an air return inlet according to an example aspect.
Figure 17:
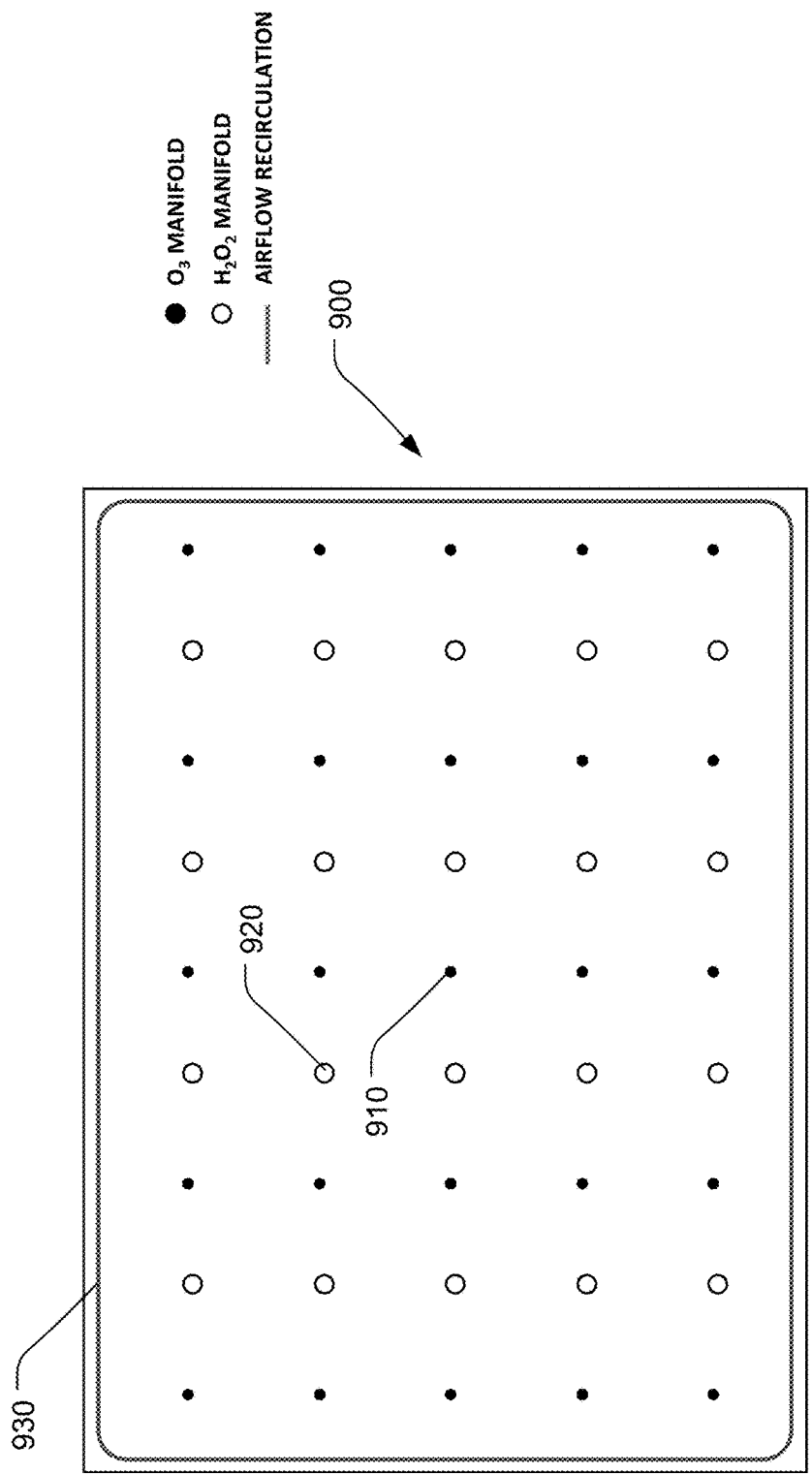
FIG. 17 is a representative illustration of an alternate possible configuration of the disposition and arrangement of ozone outlets, sterilant outlets, and air return inlets according to an example aspect.
Figure 18:
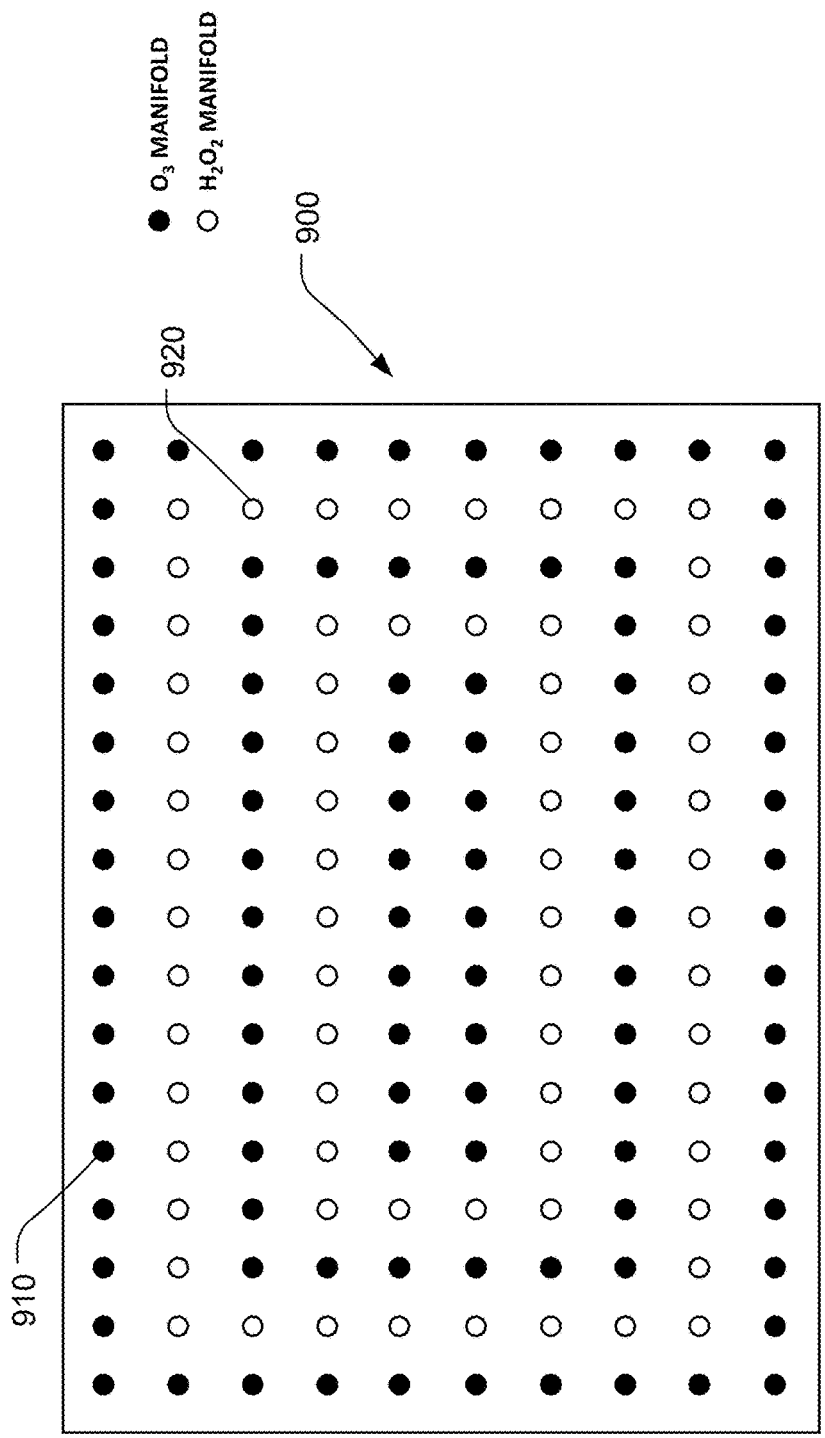
FIG. 18 is a representative illustration of an alternate possible configuration of the disposition and arrangement of ozone outlets, sterilant outlets, and an air return inlet according to an example aspect.

FIG. 13 illustrates an alternate example in which ozone outlets 910 and sterilant outlets 920 incorporated into or form a pin mat adapted to support an object being sterilized. The ozone outlets 910 and the sterilant outlets 920 are generally intermixed with each other, although the even intermixing shown in FIG. 13 should be taken as illustrative only. FIGS. 14-18 show alternate examples of intermixing that may be utilized in examples in which the ozone outlets 910 and the sterilant outlets 920 are incorporated into or form a pin mat adapted to support an object being sterilized. In all such examples, the air return inlets 930 may be located at any desired location such as those shown in FIGS. 9-18: at one or more corners (FIGS. 10, 12, 14, 16), along one or more sides (FIGS. 9, 11, 17), centrally located (FIG. 15), or at any desired location.

EXAMPLES

The sterilization device includes a global power switch, which the user presses on a user interface to provide power to a circuit board. The power switch is SPST (single pole, single throw), although a DPST (double pole, single throw) switch is also suitable. The user presses, holds, and releases the wake button (momentary switch, ON) on the user interface. The device becomes active, runs a component bit check routine, and displays a main menu. From the main menu the user can press a process info button to view sensor measurements including ambient temperature, ambient humidity, barometric pressure, battery state of charge (%), device temperature, ozone generator current, total current, and sterilization chamber pressure. The user can also press and hold an "Abort" button to run the sterilant breakdown routine from the main menu and at any time during operation. When the sterilant breakdown routine is automatically triggered through device error or by pressing the abort button the device will indicate to the user that the load is not sterile and must be reprocessed. To start a sterilization cycle the user can press, hold, and release a "Start" button. The device will then prompt the user to confirm whether the hydrogen peroxide solution was added. If the user has not added solution the device will return to the main menu. Once added and user confirmed the device will ask to confirm start of the cycle. Once cycle start has been confirmed it will automatically begin the process. During all process phases the device will display the phase number, phase name, phase time remaining, and total time remaining on the user interface. The user can also use a "Process Info" button to view all of the sensor measurements in real time.

A Phase 0 begins as the device then opens valve 1 and activates pump 1 which pulls air from the sterilization chamber and evacuates it to the external environment through a filter and breakdown catalyst. After a predetermined time the device checks the relative vacuum pressure of the sterilization chamber to confirm sufficient seal, pump, and valve operation. If the vacuum is within the specified bounds the device then continues to a Phase 1.

Phase 1 is sterilant injection. The device turns off valve 1 sealing off the external environment. During this phase all valves are off with pump 1 on. Air is pulled from the sterilization chamber and circulated through the ozone generator and separately through the nebulizing element, with each feeding back into the sterilization chamber. Ozone is not provided to the nebulizing element, such that the sterilant is not exposed to ozone until the sterilant is aerosolized and injected into the sterilization chamber. Ozone is continuously generated and injected into the sterilization chamber where it combines with the aerosolized sterilant and creates an oxidative aerosol. The injection phase is specified to reach a predetermined ozone concentration within the sterilization chamber. After a predetermined time a Phase 2 begins.

Phase 2 is sterilant exposure. The exposure phase time is determined by FDA requirements for <overkill> to reach a SAL of $10^{-6}$ otherwise the operation is identical to Phase 1. Once the exposure phase is complete a Phase 3 begins.

Phase 3 is sterilant breakdown. The device activates valve 2 which diverts air from the ozone generation branch to the breakdown catalyst branch. Pump 2 is activated with Pump 1 so that both are running simultaneously to increase the flow rate and increase the rate of sterilant decomposition. Air is continuously pulled from the sterilization chamber, circulated through the breakdown branch, and returned to the sterilization chamber for a predetermined duration to return sterilant concentrations to safe levels for human exposure (OSHA permitted exposure levels). After the predetermined time the device will indicate to the user that the process is complete, the load is sterile and ready for use. A timer will display how long the load can remain in the sterile barrier if needed prior to use. When ready the user can acknowledge the completion prompt and the sterilization chamber will vent back to ambient pressure to permit opening. After the cycle is complete the device closes and saves the data file including a log of the pass/fail determination and sensor readings then returns to standby. In one embodiment, the device maintains a partial vacuum in the sterilization chamber of between about 1 PSIV and about 2 PSIV. Increasing the vacuum rating of the device provides greater diffusion capabilities and more rapid inactivation of contaminant microorganisms. At greater vacuum levels the device could provide the capability for sterilization of products such as packaged (porous Tyvek) instruments and devices with lumens. Additionally, the improved sterilant/ozone concentrations achieved herein could provide the capacity for sterilization of packaged instruments or devices with lumens. The device may also be configured with a port to utilize supplemental oxygen or greater power for ozone production. Alternatively or additionally, the device may incorporate an oxygen concentrator to increase oxygen concentrations for improved ozone production without requiring supplemental oxygen. In these cases, process times could be reduced and throughput increased. The higher the oxygen concentration the higher the ozone concentration as the ozone is generated from oxygen molecules. The sterilant efficacy is improved with increased ozone concentration. Greater sterilant efficacy allows for more rapid inactivation of biological species permitting a shorter cycle time. Each component of the device that is in contact with the sterilant is configured to be non-reactive with the type of sterilant being used. In one embodiment, where the sterilant is a mixture of ozone and hydrogen peroxide, the oxidizing nature of the sterilant however dictates that components that come in contact with the ozone be of a material that is compatible with this gas. In one embodiment, the components may comprise one or more of stainless steel (316L), anodized aluminum, Teflon, Kynar, PEEK, EPDM, Norprene, medical grade silicone, fluorosilicone, HDPE, UHMWPE, glasses and ceramics, titanium. The device eliminates many risks associated with current chemical sterilization methods, reduces the overall logistics of chemical and thermal sterilization, and reduces the overall time needed to sterilize surgical instruments.

Figure 22:
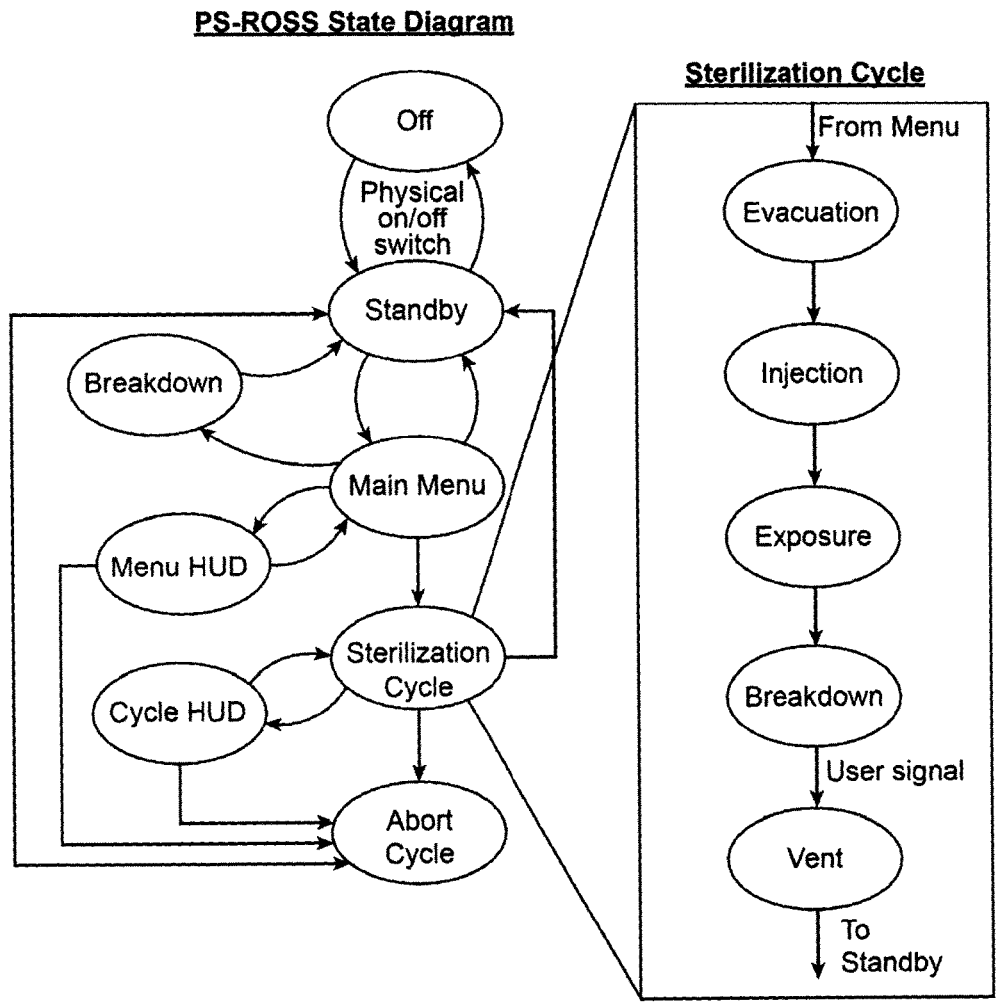
FIG. 22 is a representative illustration of a Rugged Ozone Sterilization System (ROSS) software state diagram according to another aspect of the invention.

A Rugged Ozone Sterilization System (ROSS) software state diagram is provided in FIG. 22.

Directionality of arrow indicates a one directional state transition. Various states of the sterilization cycle are shown at right. The transition between the Off and Standby states is mediated by a physical switch as opposed to a change in software state. While most of the transitions between subsequent stages in the Sterilization Cycle state are timed, the final transition is initiated by user input. Most other transitions among states in the diagram result from stimuli provided by the user.

Figure 23:
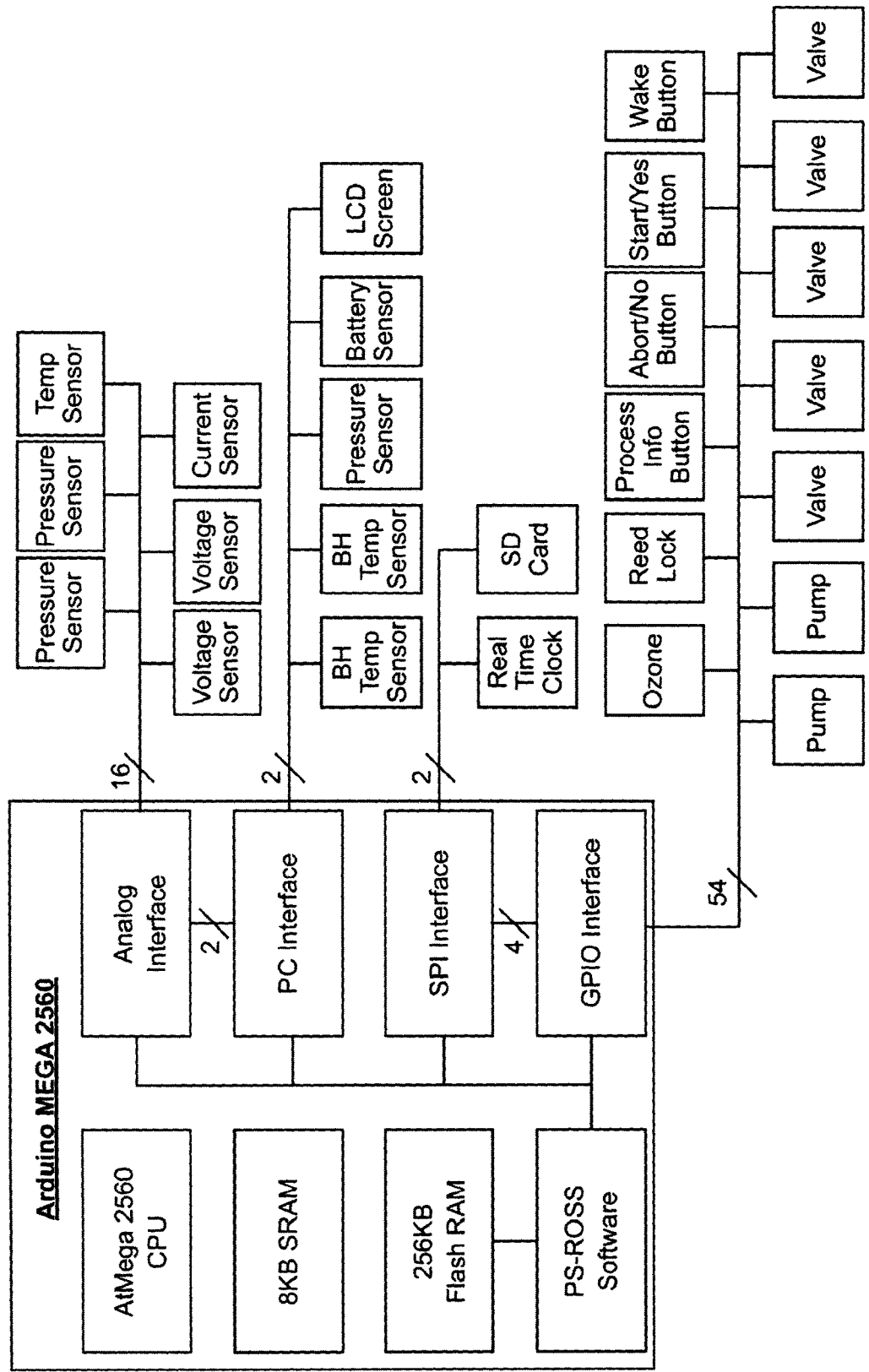
FIG. 23 is a representative illustration of a schematic of sterilization device component interface connections according to another aspect of the invention.

A schematic of sterilization device component interface connections is provided in FIG. 23.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A portable sterilization device for use with one or more sterilants, the portable sterilization device comprising:
  a sealable sterilization chamber having one or more walls defining a sealable internal volume having a height, a width, and a depth;
  a sterilant delivery device comprising an aerosolizing component and a sterilant outlet, the sterilant outlet being disposed within or at a boundary of the internal volume and oriented to disperse aerosolized sterilant into the internal volume; wherein the sterilant delivery device comprises a plurality of sterilant outlets disposed within or at the boundary of the internal volume of the sterilization chamber;
  an ozone delivery device comprising an ozone outlet disposed within or at the boundary of the internal volume such that ozone is delivered to the internal volume; wherein the ozone delivery device comprises an ozone source in fluid communication with a plurality of ozone outlets through a manifold; and
  an airflow circulation assembly comprising an ozone generation assembly having a fluid intake that receives fluid removed from the sterilization chamber through an air return in fluid communication with the ozone generation assembly;
  a control panel operable to activate the sterilant delivery device and the ozone delivery device when the sterilization chamber is sealed, whereby an oxidative aerosol sterilant is created within the internal volume by mixing of the aerosolized sterilant and the ozone in the internal volume of the sealable sterilization chamber, wherein the sterilant is substantially prevented from mixing with ozone prior to being dispersed through the sterilant outlet into the internal volume by the sterilant delivery device; and wherein at least a portion of the plurality of sterilant outlets and at least a portion of the plurality of ozone outlets are incorporated into or form a pin mat disposed within the internal volume of the sterilization chamber, the pin mat being adapted to support an object to be sterilized in the portable sterilization device.

2. The portable sterilization device of claim 1, wherein the airflow circulation assembly further comprises:
an air pump;
and
an ozone supply feed in fluid communication with the ozone generation assembly and the ozone outlet; and
wherein the air return comprises an air return opening in fluid communication with the internal volume of the sterilization chamber.

3. The portable sterilization device of claim 2, wherein the airflow circulation assembly comprises a plurality of air return openings in fluid communication with the air return and the internal volume of the sterilization chamber.

4. The portable sterilization device of claim 2, wherein the sterilant outlet, the ozone outlet, and the air return opening are located within or at the boundary of the internal volume so as to optimize formation of the oxidative aerosol sterilant within the internal volume.

5. The portable sterilization device of claim 2, wherein each of the sterilant outlet, the ozone outlet, and the air return opening are located on walls of the sealable sterilization chamber selected from the group consisting of a top wall, a bottom wall, and a side wall.

6. The portable sterilization device of claim 1, wherein the plurality of sterilant outlets are located and oriented so as to disperse an effective amount of aerosolized sterilant to an entirety of a treatment volume within the internal volume of the sterilization chamber.

7. The portable sterilization device of claim 1, wherein the plurality of ozone outlets are disposed within or at the boundary of the internal volume of the sterilization chamber, the plurality of ozone outlets being located and oriented so as to deliver ozone to an entirety of a treatment volume within the internal volume of the sterilization chamber.

8. The portable sterilization device of claim 7, wherein the plurality of sterilant outlets are located and oriented so as to disperse an effective amount of aerosolized sterilant to an entirety of the treatment volume within the internal volume of the sterilization chamber.

9. The portable sterilization device of claim 8, wherein the plurality of sterilant outlets and the plurality of ozone outlets are interspersed to facilitate mixing of the aerosolized sterilant and the ozone within the internal volume of the sterilization chamber.

10. The portable sterilization device of claim 1, wherein the sterilant comprises hydrogen peroxide.

11. The portable sterilization device of claim 1, wherein the aerosolizing component comprises a component selected from the group consisting of:
an ultrasonic nebulizer;
a mechanical nebulizer;
a piezoelectric nebulizer;
a compressive nebulizer;
a misting nozzle supplied by a pump;
a misting nozzle supplied by a linear actuator;
an ultrasonic spray nozzle;
an air atomizing nozzle;
a Venturi nozzle;
a microfluidic pin orifice;
a heat vaporizer; and
a diesel fuel injector.

12. A portable sterilization device for use with one or more sterilants, the portable sterilization device comprising:
a sealable sterilization chamber having one or more walls defining a sealable internal volume having a height, a width, and a depth;
a sterilant delivery device comprising an aerosolizing component and a sterilant outlet, the sterilant outlet being disposed within or at a boundary of the internal volume and oriented to disperse aerosolized sterilant into the internal volume; wherein the sterilant delivery device comprises a plurality of sterilant outlets disposed within or at the boundary of the internal volume of the sterilization chamber;
an ozone generation and airflow circulation assembly comprising a fluid loop for circulating fluids through the sterilization chamber, comprising:
an air return having an air return opening in fluid communication with the internal volume of the sterilization chamber;
an ozone generation assembly having a fluid intake that receives fluid removed from the sterilization chamber through the air return;
an ozone supply feed that receives ozone from the ozone generation assembly; and
a plurality of ozone outlets in fluid connection with the ozone supply feed through a manifold, the plurality of ozone outlets being disposed within or at the boundary of the internal volume of the sterilization chamber, the plurality of ozone outlets being located and oriented within or at the boundary of the sterilization chamber so as to be capable of delivering ozone to an entirety of a treatment volume of the internal volume of the sterilization chamber; and
a control panel operable to activate the sterilant delivery device and the ozone generation and airflow circulation assembly when the sterilization chamber is sealed, whereby an oxidative aerosol sterilant is created within the internal volume by mixing of the aerosolized sterilant and the ozone in the internal volume of the sealable sterilization chamber,
wherein the sterilant is substantially prevented from mixing with ozone prior to being dispersed through the sterilant outlet into the internal volume by the sterilant delivery device; and
wherein at least a portion of the plurality of sterilant outlets and at least a portion of the plurality of ozone outlets are incorporated into or form a pin mat disposed within the internal volume of the sterilization chamber, the pin mat being adapted to support an object to be sterilized in the portable sterilization device.

13. The portable sterilization device of claim 12, wherein the ozone generation and airflow circulation assembly comprises a plurality of air return openings in fluid communication with the air return and the internal volume of the sterilization chamber.

14. The portable sterilization device of claim 12, wherein the plurality of sterilant outlets are located and oriented so as to disperse an effective amount of aerosolized sterilant to an entirety of the treatment volume within the internal volume of the sterilization chamber.

15. The portable sterilization device of claim 14, wherein the plurality of sterilant outlets and the plurality of ozone outlets are interspersed to facilitate mixing of the aerosolized sterilant and the ozone within the internal volume of the sterilization chamber.

16. A sterilization method comprising:
placing an object to be sterilized within a sealable sterilization chamber of a portable sterilization device;
sealing the sterilization chamber;
aerosolizing a sterilant to create an aerosolized sterilant;
delivering the aerosolized sterilant to the sterilization chamber through a sterilant outlet disposed within or at a boundary of the sterilization chamber, wherein the sterilant is substantially prevented from mixing with ozone prior to delivery of the aerosolized sterilant to the sterilization chamber;
delivering ozone to the sterilization chamber through an ozone outlet disposed within or at the boundary of the sterilization chamber while the aerosolized sterilant is present in the sterilization chamber, whereby an oxidative aerosol sterilant is created within the sterilization chamber by mixing of the aerosolized sterilant and the ozone;
continuing to deliver the aerosolized sterilant and the ozone to the sterilization chamber for a sterilizing-effective period of time, whereby a desired assurance of sterility of the object to be sterilized is achieved;
wherein delivering ozone to the sterilization chamber comprises delivering ozone through a plurality of ozone outlets disposed within or at the boundary of the sterilization chamber and wherein delivering the aerosolized sterilant to the sterilization chamber comprises delivering the aerosolized sterilant through a plurality of sterilant outlets disposed within or at the boundary of the sterilization chamber; and
wherein the plurality of sterilant outlets and the plurality of ozone outlets are interspersed to facilitate mixing of the sterilant and the ozone within the sterilization chamber, and wherein at least a portion of the plurality of sterilant outlets and at least a portion of the plurality of ozone outlets are incorporated into or form a pin mat disposed within the internal volume of the sterilization chamber, the pin mat being adapted to support the object to be sterilized in the portable sterilization device.

17. A portable sterilization device for use with one or more sterilants, the portable sterilization device comprising:
a sealable sterilization chamber having one or more walls defining a sealable internal volume having a height, a width, and a depth;
a sterilant delivery device comprising an aerosolizing component and a sterilant outlet, the sterilant outlet being disposed within or at a boundary of the internal volume and oriented to disperse aerosolized sterilant into the internal volume;
an ozone delivery device comprising an ozone outlet disposed within or at the boundary of the internal volume such that ozone is delivered to the internal volume; and
a control panel operable to activate the sterilant delivery device and the ozone delivery device when the sterilization chamber is sealed, whereby an oxidative aerosol sterilant is created within the internal volume by mixing of the aerosolized sterilant and the ozone in the internal volume of the sealable sterilization chamber,
wherein the sterilant is substantially prevented from mixing with ozone prior to being dispersed through the sterilant outlet into the internal volume by the sterilant delivery device;
wherein the sterilant delivery device comprises a plurality of sterilant outlets disposed within or at the boundary of the internal volume of the sterilization chamber, the plurality of sterilant outlets being located and oriented so as to disperse an effective amount of aerosolized sterilant to an entirety of the treatment volume within the internal volume of the sterilization chamber;
wherein the plurality of sterilant outlets and the plurality of ozone outlets are interspersed to facilitate mixing of the aerosolized sterilant and the ozone within the internal volume of the sterilization chamber; and
wherein at least a portion of the plurality of sterilant outlets and at least a portion of the plurality of ozone outlets are incorporated into or form a pin mat disposed within the internal volume of the sterilization chamber, the pin mat being adapted to support an object to be sterilized in the portable sterilization device.

\* \* \* \* \*